United States Patent
Kidman et al.

(10) Patent No.: US 11,083,825 B2
(45) Date of Patent: Aug. 10, 2021

(54) MEDICAL/SURGICAL LAVAGE UNIT INCLUDING INTERNAL RIBS THAT EXTEND INTO A VOID SPACE OF A SUCTION TUBE ATTACHED TO THE LAVAGE UNIT

(71) Applicant: Stryker Corporation, Kalamazoo, MI (US)

(72) Inventors: Beau Kidman, Kalamazoo, MI (US); Ivan Matos Perez, Juana Diaz, PR (US); Chris Hunke, Dallas, TX (US); Neal Johnston, Dallas, TX (US)

(73) Assignee: Stryker Corporation, Kalamazoo, MI (US)

( * ) Notice: Subject to any disclaimer, the term of this patent is extended or adjusted under 35 U.S.C. 154(b) by 480 days.

(21) Appl. No.: 15/962,223

(22) Filed: Apr. 25, 2018

(65) Prior Publication Data

US 2018/0236145 A1    Aug. 23, 2018

Related U.S. Application Data

(63) Continuation of application No. 14/728,030, filed on Jun. 2, 2015, now Pat. No. 9,987,403, which is a continuation of application No. PCT/US2013/073272, filed on Dec. 5, 2013.

(60) Provisional application No. 61/733,989, filed on Dec. 6, 2012.

(51) Int. Cl.
*A61M 1/00* (2006.01)
*A61M 3/02* (2006.01)

(52) U.S. Cl.
CPC .......... *A61M 1/0064* (2013.01); *A61M 3/022* (2014.02); *A61M 3/0208* (2014.02); *A61M 3/0258* (2013.01); *A61M 3/0283* (2013.01); *A61M 2206/11* (2013.01); *A61M 2210/02* (2013.01)

(58) Field of Classification Search
CPC ............ A61M 1/0064; A61M 2206/11; A61M 2210/02; A61M 3/0208; A61M 3/022; A61M 3/0258; A61M 3/0283
See application file for complete search history.

(56) References Cited

U.S. PATENT DOCUMENTS

| | | | |
|---|---|---|---|
| 5,046,486 A | 9/1991 | Grulke et al. |
| 5,147,292 A | 9/1992 | Kullas et al. |
| 5,460,604 A | 10/1995 | Arnett et al. |
| 5,941,851 A | 8/1999 | Coffey et al. |
| 6,022,329 A | 2/2000 | Arnett et al. |
| 7,153,287 B2 | 12/2006 | Henniges et al. |
| 9,987,403 B2 | 6/2018 | Kidman et al. |
| 2002/0173746 A1 | 11/2002 | McMahon et al. |

FOREIGN PATENT DOCUMENTS

| | | |
|---|---|---|
| JP | H02230977 A | 9/1990 |
| WO | 2014/043475 A1 | 3/2014 |

OTHER PUBLICATIONS

English language abstract retrieved from Espacenet on Nov. 16, 2017 for JPH02230977A, which was also published as U.S. Pat. No. 5,046,486A.

PCT "International Search Report and Written Opinion" for PCT/US2013/073272, dated May 13, 2014.

*Primary Examiner* — Kai H Weng
(74) *Attorney, Agent, or Firm* — Howard & Howard Attorneys PLLC

(57) ABSTRACT

A medical/surgical lavage unit including internal ribs that extend into a void space of a suction tube attached to the lavage unit.

21 Claims, 25 Drawing Sheets

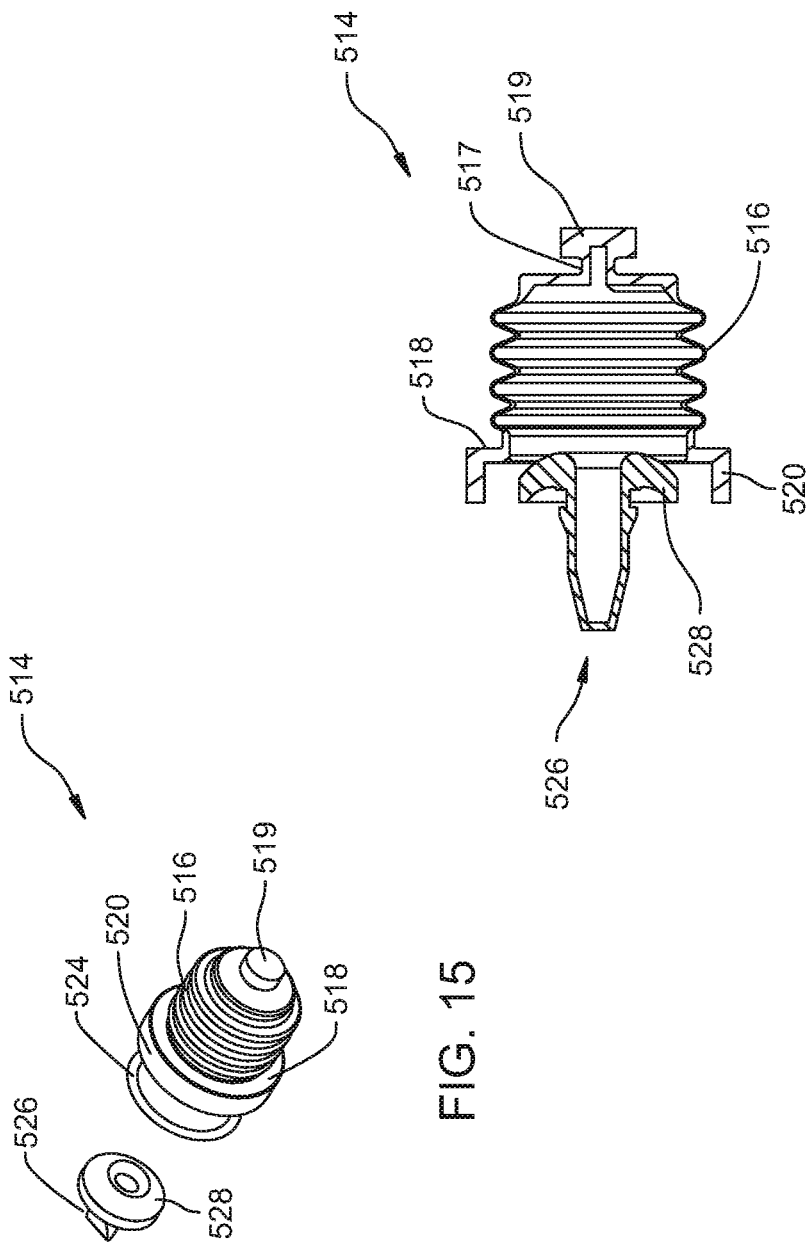

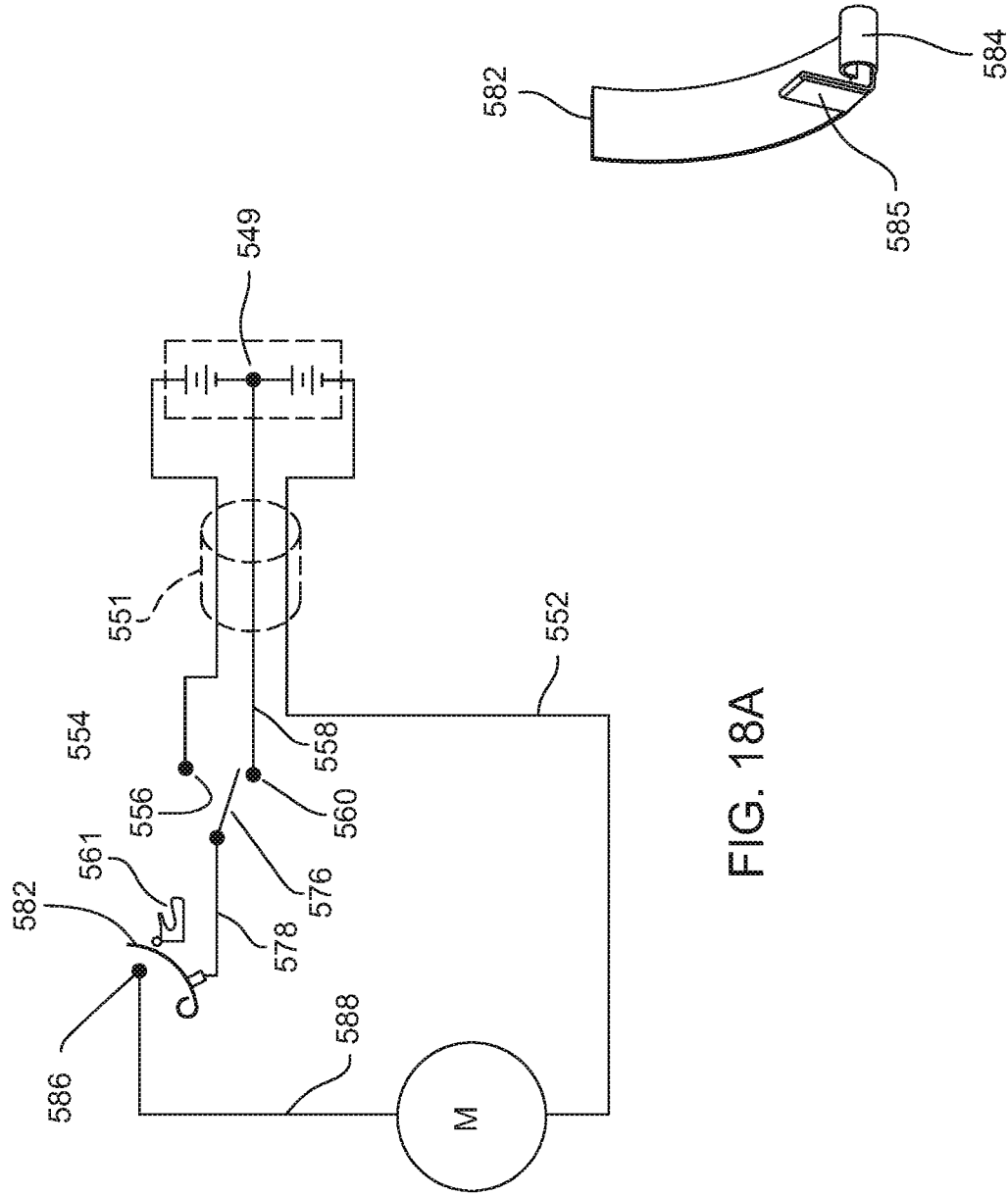

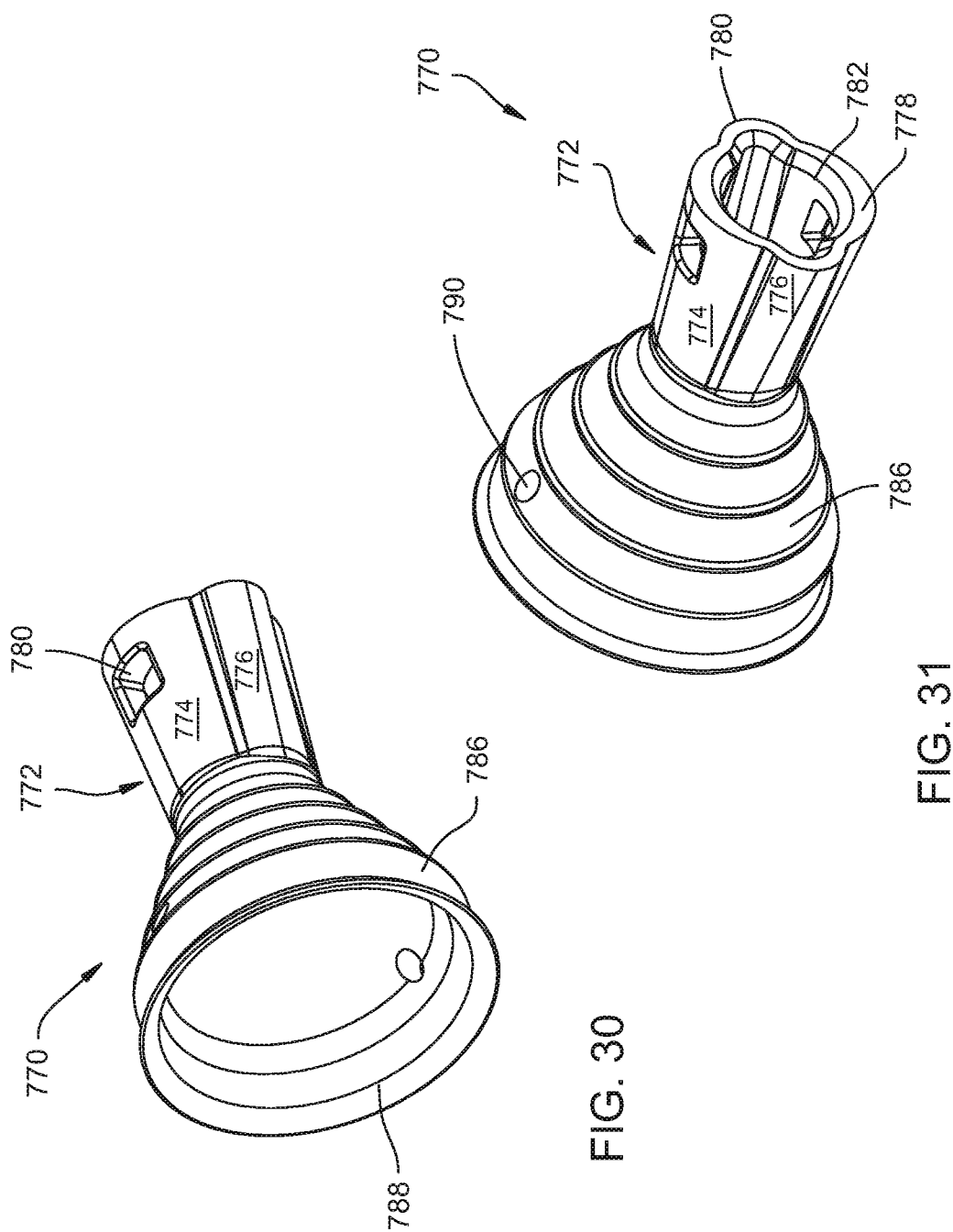

MEDICAL/SURGICAL LAVAGE UNIT INCLUDING INTERNAL RIBS THAT EXTEND INTO A VOID SPACE OF A SUCTION TUBE ATTACHED TO THE LAVAGE UNIT

CROSS-REFERENCE TO RELATED APPLICATIONS

This application is a continuation of U.S. patent application Ser. No. 14/728,030, filed on Jun. 2, 2015, which is a Continuation of PCT/US2013/073272 filed on Dec. 5, 2013, which claims priority from U.S. Provisional Application No. 61/733,989 filed on Dec. 6, 2012, each of which is hereby incorporated by reference in its entirety.

BACKGROUND

In many surgical and medical procedures, a lavage unit is employed to deliver fluid to a particular location on or in the body of a person receiving medical attention. For example, during orthopedic surgery, a lavage unit may be employed to deliver pressurized pulses of water or saline solution to an exposed surface of the bone in order to clean the bone. There are also some non-surgical procedures performed which likewise make it desirable to apply pulses of water to a specific site on an individual's skin. Thus, if an individual is suffering from some type of bed sore or some other type of skin wound, it is a common practice to use a lavage unit to clean the wound prior to applying a dressing to the wound.

A common type of medical/surgical lavage unit includes a handpiece to which a tip assembly is selectively attached. Often, inside the handpiece is a small pump that periodically delivers a quantity of pressurized fluid. Alternatively, the pressurized fluid is delivered to the handpiece from an external pump. The fluid is discharged through a discharge tube integral with the tip assembly to the selected site on or in the patient. These lavage units deliver fluid in pressurized pulses for two reasons. One reason is that fluid pulses quickly strike the site to which they are applied and leave the site; this action serves to foster the desirable removal of debris from the site. Secondly, the discrete fluid pulses do not obstruct the view of the site as much as it can be obstructed when exposed to a continuous flow of pressurized fluid.

Most lavage units, in addition to having a conduit through which the sterile fluid is discharged, have a conduit through which the discharged fluid is removed from the site to which it is applied. Typically, the fluid is initially withdrawn from the site through a suction tube, also part of the tip assembly. The fluid, as well as any debris in the fluid stream, then flow through a conduit integral with the handpiece. The handpiece suction conduit is connected to a second suction tube that is connected to a suction system separate from the irrigator. Thus, given their ability to essentially simultaneously clean a site on a patient and remove the debris generated by the cleaning process, it should be readily apparent why irrigators have become useful tools for facilitating many medical and surgical procedures.

Further, it is the common practice to manufacture both the handpiece and tip assembly of lavage unit as use-once items. One reason these units are use-once is economics. The cost of forming these devices out of sterilizable components and then sterilizing the devices after each use can be greater than the cost of providing a quantity of use-once device. A second reason these units are use-once items is related to weight. The weights of components forming a handpiece manufactured to be sterilizable are greater than the weights of comparable components forming a use-once handpiece. During a procedure, such as bone cleaning, it may be necessary to hold the lavage unit steady for time periods that run into the minutes. Making the lavage unit as light as possible reduces the muscle fatigue of the individual required to hold the unit steady for an extended periods of time.

Applicant's U.S. Pat. Nos. 6,022,329 and 7,153,287, both of which are explicitly incorporated herein by reference, disclose use-once lavage units. In these patents and in other publications, lavage units are sometimes referred to as irrigators.

The lavage units of the incorporated by reference patents work reasonably well. Still, sometimes with these lavage units, as well as other lavage units the suction tubes integral with the tip assemblies clog with debris. This means use of the unit has to be interrupted in order to either clear the clog or to attach a replacement tip assembly. Taking the time to perform either of these procedures runs contrary to the goal of modern medical practice, that a procedure should be performed as quickly as possible so as to minimize the time the patient is both held under anesthesia or has internal body tissue that is exposed to the ambient environment.

Further as with any product, there is always a desire to hold the costs of product to a minimum. One area in which this has affected lavage handpiece design is the trigger. The trigger is the manual member the practitioner depresses to selectively actuate the pump motor. In some situations, the practitioner may want to rapidly control the on/off discharging of the lavage fluid by the pump. When this type of control is required, the trigger needs to operate as a momentary contact switch. In some situations the practitioner may want the pump to remain on for an extended period of time, 30 seconds or more. If the trigger is of the momentary contact variety, the practitioner has to exert mental and physical effort ensuring the trigger remains in the on state, the trigger should operate as a switch that is selectively toggled on and off. This is a reason why it would be useful to provide a lavage unit with a toggle switch that is toggled between the on and off states. However, sometimes, in same procedure the practitioner may want the trigger to function as both as momentary contact switch on one phase of the procedure and, in another phase of the procedure, as a toggle switch. To date it has proven difficult to provide a use-once lavage handpiece with a trigger that can operate both as a contact switch and a toggle switch.

SUMMARY OF THE DISCLOSURE

This disclosure is directed to a new and useful lavage unit. The lavage unit of this disclosure includes both a handpiece with a pump and a tip assembly that extends distally forward from the handpiece.

Both the handpiece and tip assembly of this disclosure are formed to reduce the likelihood that debris entrained in the suction flow from patient clog the suction flow path. Specifically, the tip assembly includes an irrigation tube disposed inside the suction tube. These two tubes, and their complementary lumens are not coaxial. This feature of the disclosure increases the cross section distance of the axes of the suction lumen. Internal to the handpiece the suction path includes a pair of bores. These bores are axially offset. Further these bores are not circular. These bores overlap is such a way as to present a relatively wide flow through path. This feature of the disclosure both reduces the likelihood of clogging and the low cost manufacture of the pump.

The handpiece of this disclosure includes a multi-position trigger. Normally, the trigger is in the off state. The trigger can be displaced an initial distance. When the trigger is displaced the initial distance, the trigger functions as a momentary contact switch; the release of the trigger immediately returns the trigger to the off state. The trigger can also be displaced a second distance that is greater than the first distance. When the trigger is displaced the second distance, the trigger engages a complementary stop. The trigger stays in static on state position. The handpiece pump remains in the on state until an addition effort is made to displace the trigger. The displacement of the trigger to the third position returns the trigger to the off state. Thus the trigger of this disclosure operates as both a momentary contact switch and a toggle switch that can be set to a constant on state or constant off state.

In some but not all versions of the disclosure, the displacement of the trigger to the second position causes the trigger to engage and be held in position by a stop. The stop in some versions of the disclosure is a feature formed in one of the shell members from which the housing of the handpiece is formed.

BRIEF DESCRIPTION OF THE DRAWINGS

The disclosure is pointed out with particularity in the claims. The above and further features and advantages of this disclosure are understood from the following Detailed Description taken in conjunction with the accompanying drawings in which

FIG. 15 is a perspective view of the bellows and valve internal to the handpiece;

FIG. 16 is a cross-sectional view of the valve and bellows internal to the handpiece;

FIG. 18A is a schematic and diagrammatic depiction of the electrical connections of the handpiece to the power supply;

FIG. 18B is a perspective view of the contact associated with the on/off trigger of the handpiece;

FIG. 30 is a perspective view of the front of the spray shield;

FIG. 31 is a perspective view of the rear of the spray shield;

DETAILED DESCRIPTION

I. Overview

Figure 1:
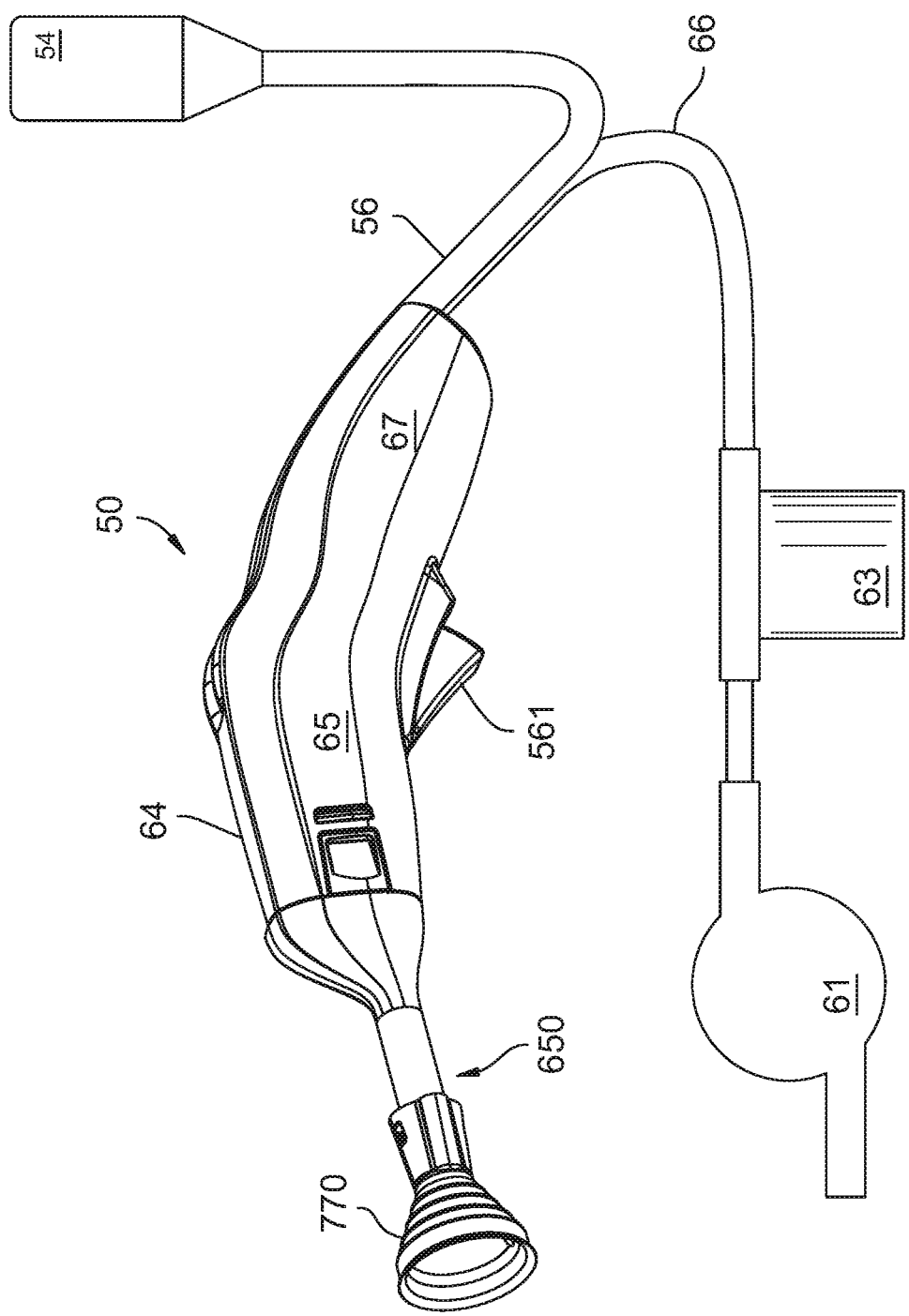
FIG. 1 is a perspective view of a lavage unit of this disclosure.
Figure 2:
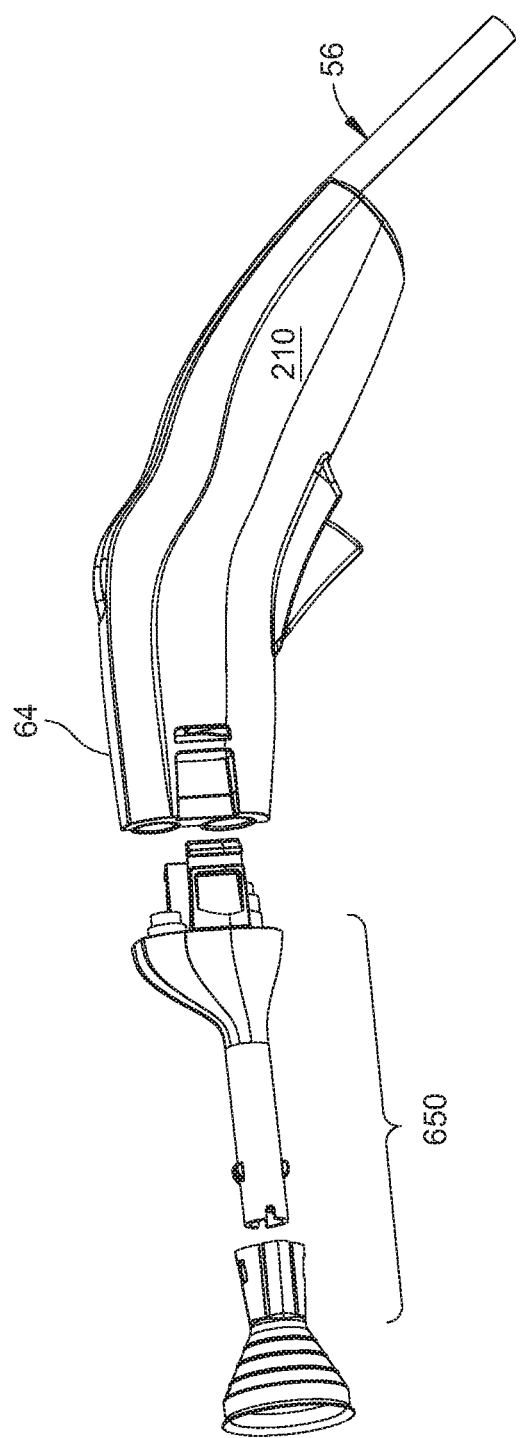
FIG. 2 is an exploded perspective view of the lavage unit.
Figure 3:
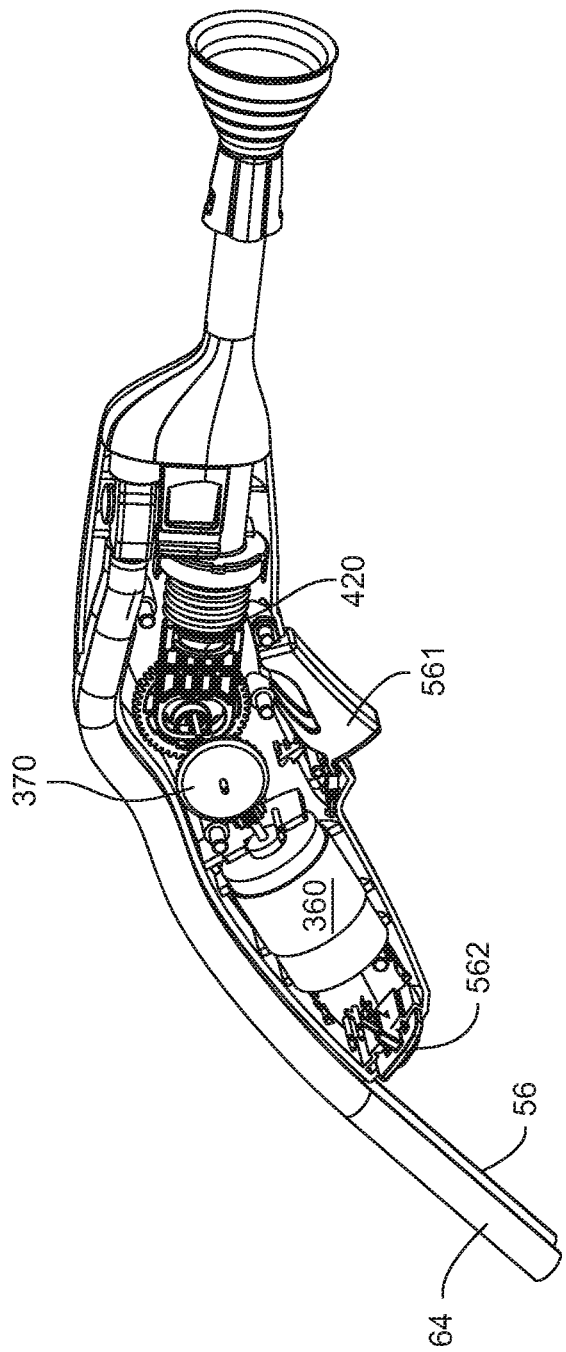
FIG. 3 is a cutaway view depicting the interior of the lavage unit handpiece.

FIGS. 1-3 depict the basic components of a lavage unit 50 of this disclosure. Lavage unit 50 includes a handpiece 64 to which a tip assembly 650 is removably attached. An irrigation tube 56 runs from a source of irrigating fluid 54 to the handpiece 64. A suction tube 66 is mounted to the handpiece 64. Suction tube 66 extends proximally to both a waste collection container 63 and a suction source 61. (Here "proximally" means towards the practitioner holding handpiece 64, away from the patient to which the tip assembly 650 is applied. "Distally" means away from the practitioner and towards the patient.) Internal to the handpiece 64 is a pump 420 to which the distal end of irrigation tube 56 is connected. Pump 420 is driven by a motor 360. The on/off state of the motor 360 is controlled by a trigger 561 that is pivotally mounted to the underside of the handpiece 64. The speed at which the motor 360 and, by extension the rate at which pump 420 operates, is controlled by a speed setting switch 562. Switch 562 is slidably mounted to the proximal end of the handpiece 64.

Figure 28:
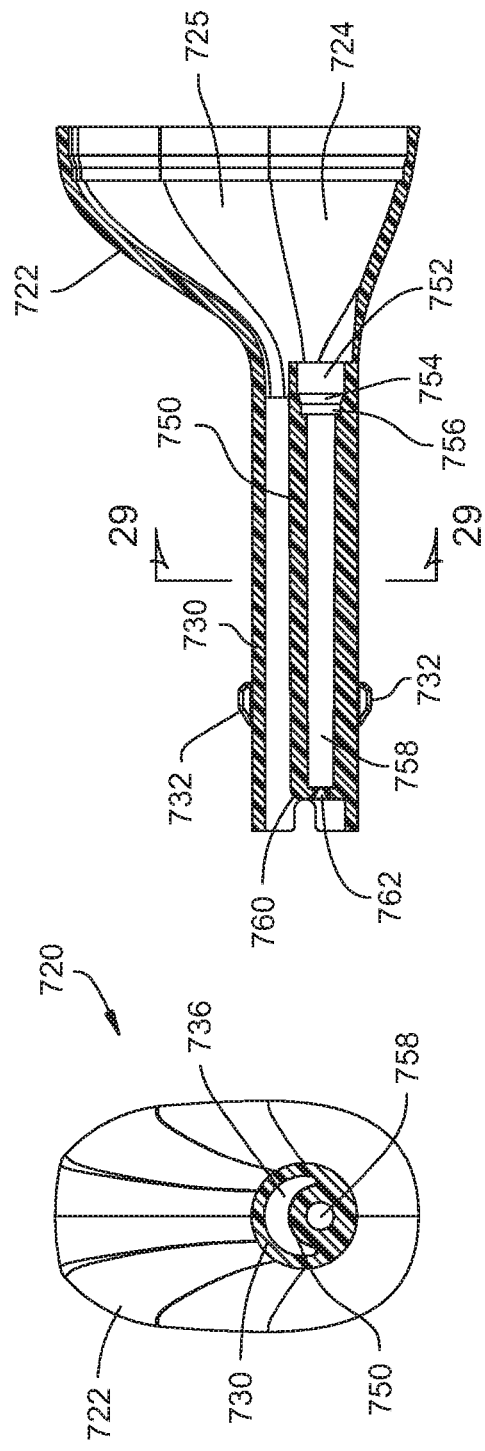
FIG. 28 is a cross sectional view of the body of the tip assembly along a plane that extends longitudinally through the body.

Tip assembly 650 includes a rigid irrigation tube 750, seen in FIG. 28. Irrigation tube 750 is disposed inside a suction tube 730. A spray shield 770 is removably disposed over suction tube 730. When the tip assembly 650 is attached to the handpiece 64, a first fluid communication path is established between the outlet port of pump 420 and irrigation tube 750. A second fluid communication path is established between the proximal end of suction tube 730 and suction tube 66 that is attached to and extends from the handpiece 64.

II. Handpiece

Figure 4:
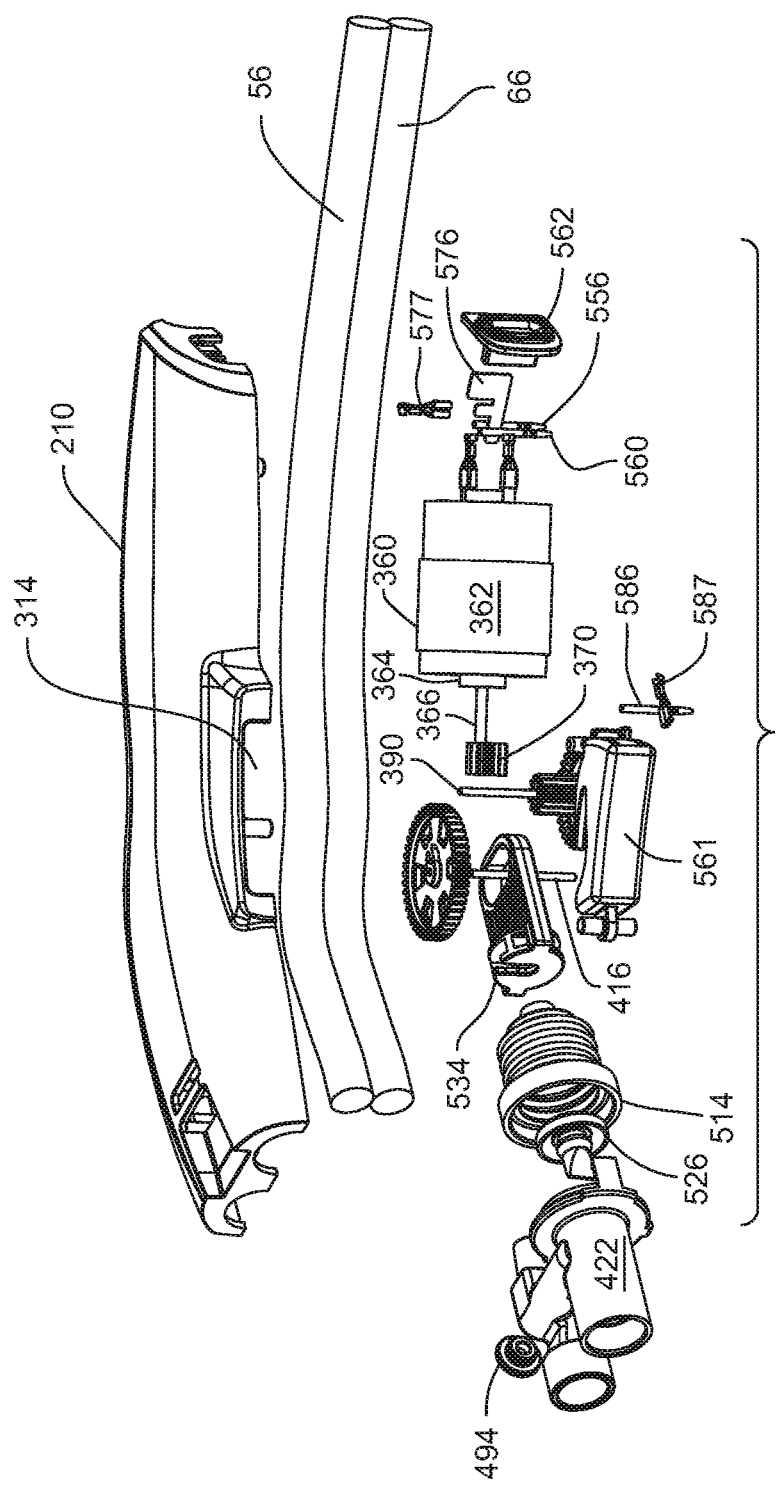
FIG. 4 is a exploded view of the components internal to the handpiece.
Figure 5:
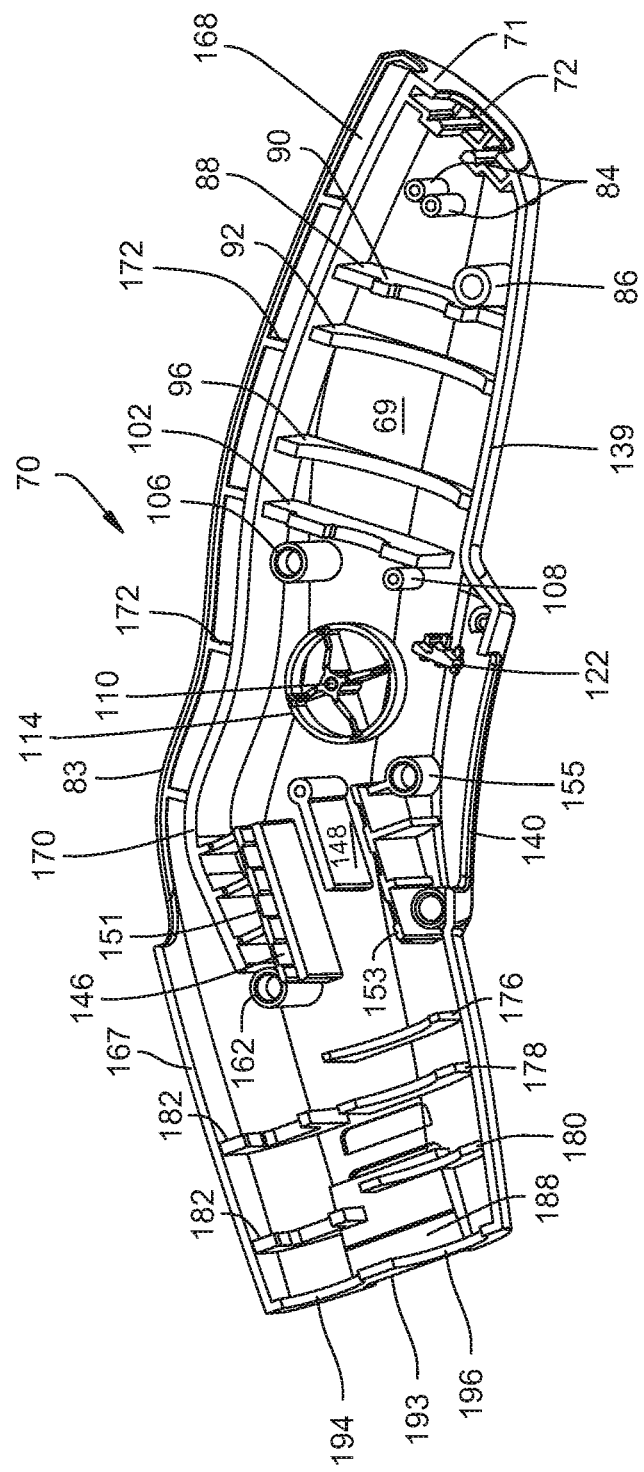
FIG. 5 is a perspective view of the inside of the right side shell of the handpiece.

Handpiece 64 includes a right and left shells 70 and 210, respectively, as seen in FIGS. 4 and 5. Collectively, shells 70 and 210 form the housing or body of the handpiece 64. The shells 70 and 210 have proximal and distal sections that have proximal to distal longitudinal axes that are not linear. Thus, the proximal sections of the shells collectively form a handgrip 65 of handpiece 64. The distal sections of the shells collectively form a barrel 67 of the handpiece 64. Shells 70 and 210 are formed out of plastic such as ABS.

Figure 6:
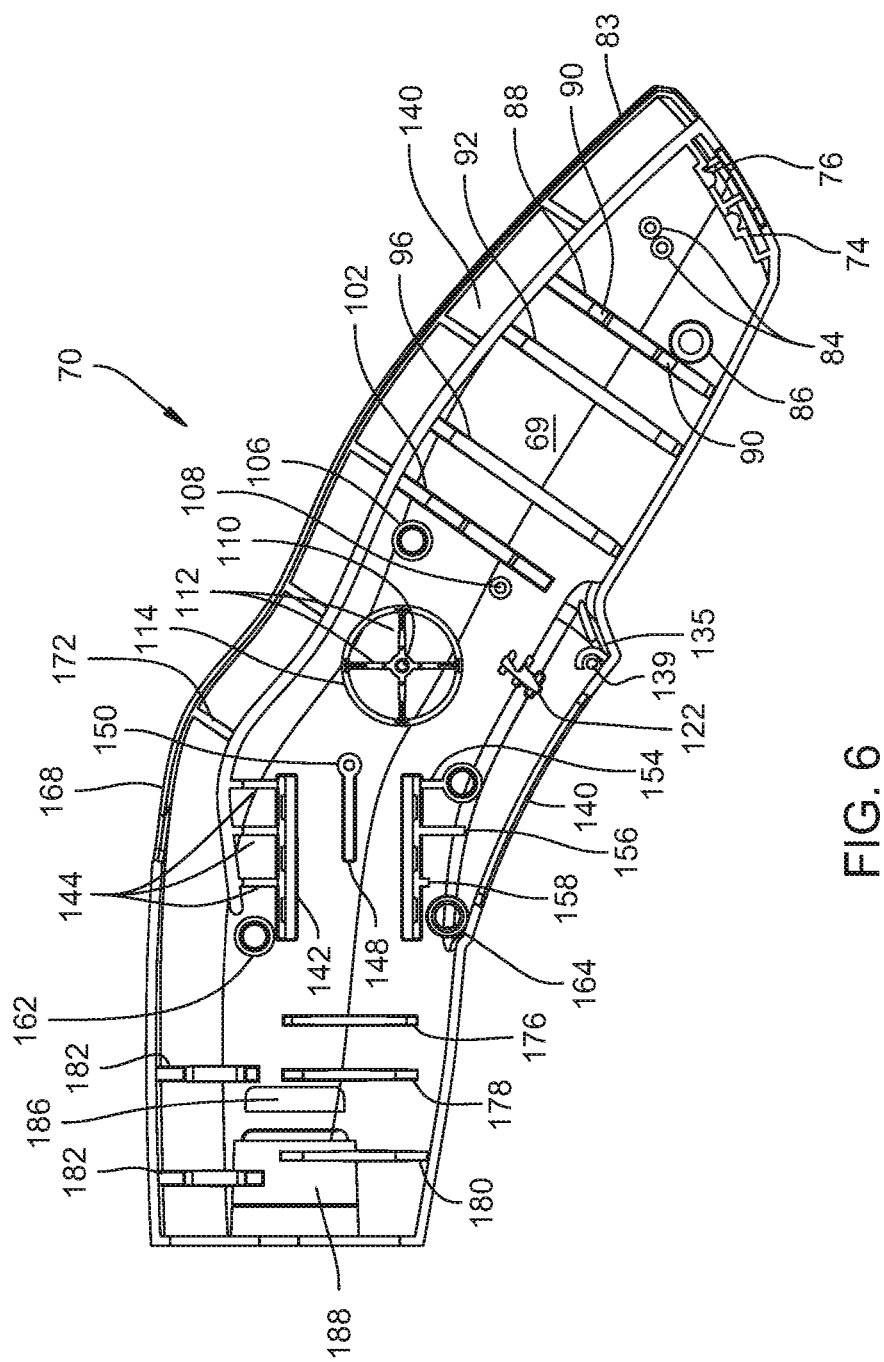
FIG. 6 is a plan view of the inside of the right side shell.

As seen in FIGS. 5 and 6, right shell 70 is formed so as to have a base 69. A rectangular notch 72 in the proximalmost rim, rim 71, of the shell 70. Two brackets 74 and 78 extend upwardly from the shell base so as to partially extend into the space internal to shell 70 subtended by notch 72. Bracket 74, as seen in FIG. 6A, is L-shaped in that it has a minor portion that extends distally inwardly from the shell proximalmost rim 71. Brackets 74 and 78 are generally planar. At the ends of brackets 74 and 78 adjacent each other each bracket 74 and 78 is formed with a step 75 and 79, respectively. Each step 75 and 79 is located distally forward of the bracket 74 and 78, respectively, from which the step extends. A rib 76 and 80 protrudes proximally from each step 75 and 79, respectively. Ribs 76 and 80 are convex in shape. It should be understood that steps 75 and 79 are spaced apart from each other.

Forward of steps 75 and 79 two bosses 84 extend upwardly from the inner surface of the shell base. Each boss 84 is formed with a closed end bore (not identified). Bosses 84 are located towards the upper rim, rim 83 of the shell 70. A boss 86 extends upwardly from the inner surface of the shell base. Boss 86 is located below and distally forward of bosses 84. A closed end bore (not identified) extends inwardly from the exposed face of boss 86.

Four ribs 88, 92, 96, and 102 extend upwardly from the shell base. Ribs 88, 92, 96, and 102 are located forward of boss 86. The ribs 88, 92, 96 and 102 are generally parallel to each other and extend laterally across the shell base, from a location adjacent the top of the shell towards the lower rim 139. Rib 88 is formed to have two spaced apart tabs 90 that extend upwardly from the main body of the rib. Between tabs 90, rib 88 has a top surface (not identified) that is concave in shape. Each of ribs 92 and 96 has an inwardly curved face such that the face serves as the base of a notch defined by the rib (faces and notches not identified). Rib 102 generally protrudes above the inwardly curved faces of ribs 92 and 96. Rib 102 is further formed to have a U-shaped notch (not identified).

Two bosses 106 and 108 extend upwardly from the shell base. Bosses 106 and 108 are both located forward of rib 102. Boss 106 is located towards the upper rim of the shell 70. The boss 108 is located towards the lower rim of the shell 70. Boss 108 is smaller in diameter than boss 106. Both bosses 106 and 108 are formed with closed end bores, (not identified). Boss 108 is of smaller diameter than boss 106.

Forward of bosses 106 and 108, the right shell 70 is formed with a boss 110. Boss 110 is located between and distally forward of bosses 106 and 108. The boss 110 is formed with a closed end bore, (not identified). Four equiangularly spaced apart reinforcing webs 112 project radially outwardly from the outer surface of the boss 110. The webs 112 taper downwardly from the outer face of the boss 110. The webs 112 extend to a ring 114 that extends upwardly from the inner surface of the base of shell 70. The ring 114 extends above the surface of shell 70 a distance less than the distance boss 110 extends above the shell.

Figure 6B:
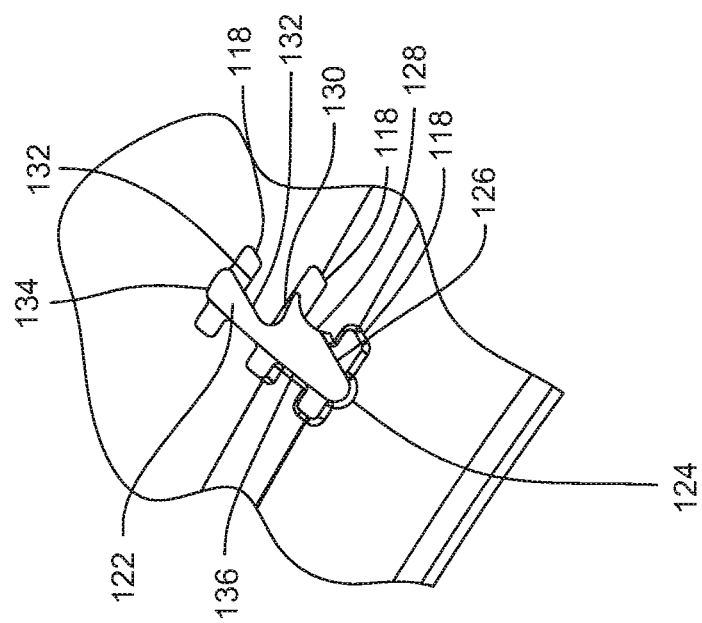
FIG. 6B is a plan view of the trigger assembly bracket depicted in FIG. 6.
Figure 6A:
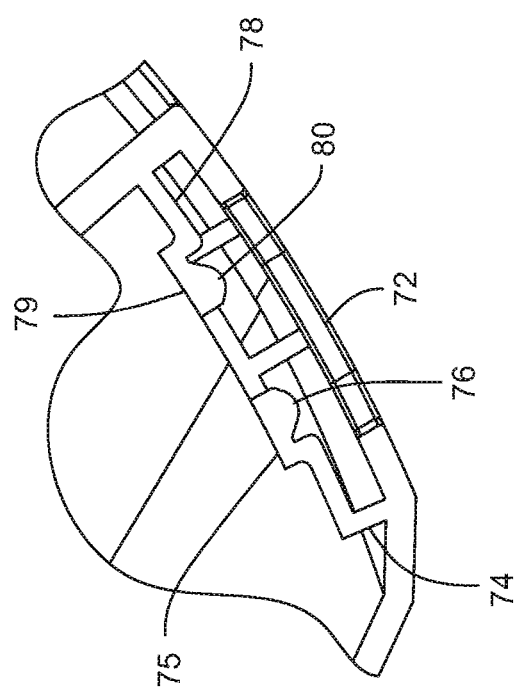
FIG. 6A is an enlarged view of the portion of the handpiece housing forming shell indicating where the speed control switch is seated.

A bracket 122, seen best in FIG. 6B, is also integrally formed with the right shell 70. The bracket 122 seats on three parallel bars 118 that project outwardly from the inner surface to the shell 70. Bars 118 and bracket 122 are both located between and below boss 108 and boss 110. The bracket 122 is generally elongated shaped structure such that the major axis of the bracket, the longitudinal axis, extends along a line that extends between the lower and upper rims of the shell. Bracket 122 is formed so the lower end of the bracket has a convex shaped bottom surface 124. Extending proximally and upwardly from surface 124 the bracket has a first proximal side surface 126 that generally tapers proximally and upwardly away from surface 124. Above surface 126, the bracket has a second proximal side surface 128 that is convex in shape. Side surface 128 thus defines a notch in the bracket 122. Above surface 128, the bracket is shaped to define a step surface 130. The step surface 130 extends generally distally forward from the outer top edge of the second side surface 128. Step surface 130 is concave in shape. The bracket 122 is further formed to have a third proximal side surface 132. The third proximal side surface 132 extends upwardly and proximally away from the distal end of step surface 130. The third proximal side surface 132 merges into a top surface 134. The top surface 134 is generally semicircular in shape. A distal side surface, surface 136, extends downwardly from top surface 134 to bottom surface 124.

Below and forward of bracket 122, the lower rim 139 of the right side shell 70 is formed to define an elongated notch 140. Notch 140 is present where the shell bends from forming the grip portion 67 of the handpiece to the barrel portion 65. Proximal to notch 140 a pin 135 extends upwardly from shell base 69. Pin 135 is spaced inwardly from the lower rim 139 of the shell. A J-shaped bracket 137 extends outwardly from the shell base 69. Bracket 137 substantially but not completely surrounds pin 135. Right side shell 70 is shaped so that bracket 137 does not surround the distally facing surface of pin 135.

Above notch 140, three parallel rails 142, 148 and 152 extend upwardly from the inner surface of the base of shell 70. The rails 142, 148 and 152 are located in the portion of the shell 70 that form the barrel section of the handpiece 64. Rail 142 is located towards the upper end of shell 70. Rail 152 is located towards the lower end of the shell. Rail 148 is located between rails 142 and 152. The rails 142, 148 and 152 each have a proximal end that is located on a common line that extends laterally across the shell 70. Webs 142 and 152 extend distally further than rail 148. Three webs 144 extend upwardly from the inner surface of the base or shell 70. Each web 144 also extends outwardly from the top surface of rail 142. A rim 146 protrudes outwardly from the outer faces of web 142. More specifically, the rim 146 protrudes outwardly from the upper portion of the rail 142.

A cylindrical boss 150 is formed integrally with rail 148. Boss 150 is located at the proximal end of the rails 148 so as to be located rearwardly of rails 142 and 152. The boss 150 is formed with a closed end bore, (not identified). A rim 153 extends outwardly from the bottom of the exposed face of rail 152. Rims 146 and 153 are both formed with indentations 151 identified only on rim 146. Indentations 151 extend inwardly from the opposed surfaces of rims 146 and 153 that face each other.

Three webs 154, 156 and 158 extend upwardly from the shell base 69 and outwardly from the bottom face surface of the rail 152. Web 154 is located adjacent the proximal end of the rail 152. The shell 70 is formed so that a cylindrical boss 155 extends upwardly from the base of the shell. Boss 155 is integral with the end of web 154 spaced from rail 152. A closed end bore (not identified) extends from the exposed face of boss 155. Web 156 is located forward web 154 and is longer in length (distance projecting from rail 152) than web 154. Web 158 is the distal most located web and is shorter in length than web 154. A step 160 projects outwardly from the bottom of rail 152. Step 160 is similar in shape to step 146 of rail 142.

Two additional cylindrical bosses, bosses 162 and 164, extend upwardly from inner surface of shell 70. The boss 162 is located immediately above the distal end of rail 142. Boss 164 is located immediately below the distal end of rail 152. Not identified are the closed end bores formed in bosses 162 and 164.

Right shell 70 is further formed to define a notch 168 in the top located rim 167. The notch 168 extends from the proximal end of the shell 70 along the whole of the grip-forming portion 67 of the shell. Notch 168 also extends a short distance along the barrel-forming portion 65 of the shell 70. The shell 70 is further formed to define a ledge 170 that projects outwardly from the shell base 69 a short distance below notch 168. The ledge 170 occupies the space below the notch 168 and extends a short distance, approximately 1 cm forward of the distal end of the notch. Webs 172 extend to the ledge 170. Plural webs 172, five shown, extend upwardly from the shell base so as to extend between the upper rim and ledge 170. Webs 172 have concave faces. More particularly ledge 170 and webs 172 are dimensioned to compression hold the suction tube 66 in the space above the ledge.

In the depicted version of the disclosure, bracket 76 extends downwardly from the undersurface of ledge 170. Webs 88, 92, 96, 102 and 144 also each extend downwardly from the undersurface of the ledge 170.

Three parallel yokes 176, 178, and 180 extend upwardly from the inner surface of shell 70. Yokes 176, 178 and 180 are located forward of rails 142 and 152 and have co-linear lateral axes that are along a line located between rails 142 and 152. The yokes 176, 178 and 180 are generally in the form of planar structures. Each yoke 176, 178 and 180 is shaped to define a notch that has an arcuate base, (notches not identified). Two additional yokes 182 also extend upwardly from the inner surface of shell 70. Yokes 182 are parallel with each other. Each yoke 182 extends downwardly from the inner surface of the upper rim of the shell. The most proximal of the yokes 182 is approximately longitudinally aligned with yoke 178. The distal of the two yokes 182 is located forward of yoke 180. Each yoke 182 is formed to define a notch with a curved base (notches not identified).

The base of the right shell 70 is formed to have a through opening 186. Through opening 186 is located between yokes 178 and 180. The through opening 186 is generally rectangularly shaped. In the depicted version of the disclosure the proximal most corners of through opening 186 are rounded. The major axis of the through opening 186 is parallel to the longitudinal axes of yokes 178 and 180. Spaced forward of the through opening 186, the right shell is formed to have a recessed panel 188, the distal end of which is only partially seen in FIG. 5. The shell 70 is shaped so that panel 188 extends proximally rearward from the distal end of the shell. Panel 188 thus defined a recess in the outer surface of shell base 69. This recess leads into the inside of the shell 70.

The distally directed rim of shell 70 is formed with two semi-circular notches, notches 194 and 196.

Figure 7:
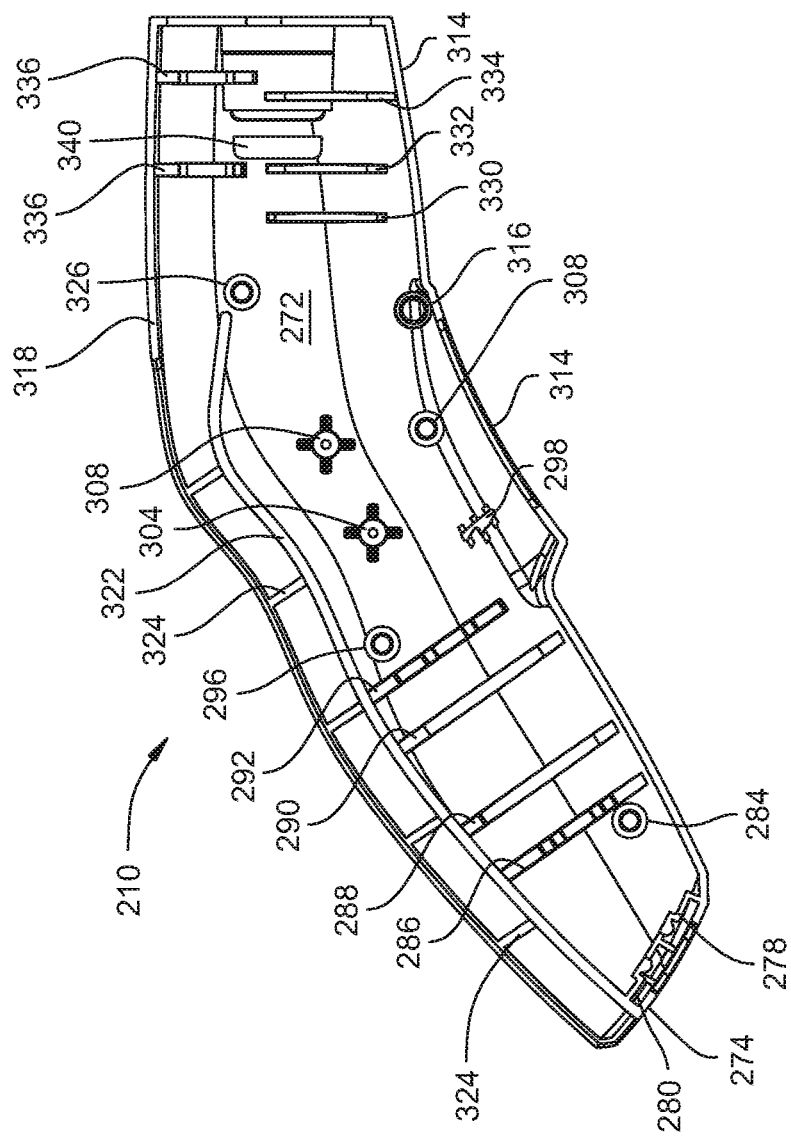
FIG. 7 is a plan view of the left side shell of the handpiece.
Figure 8:
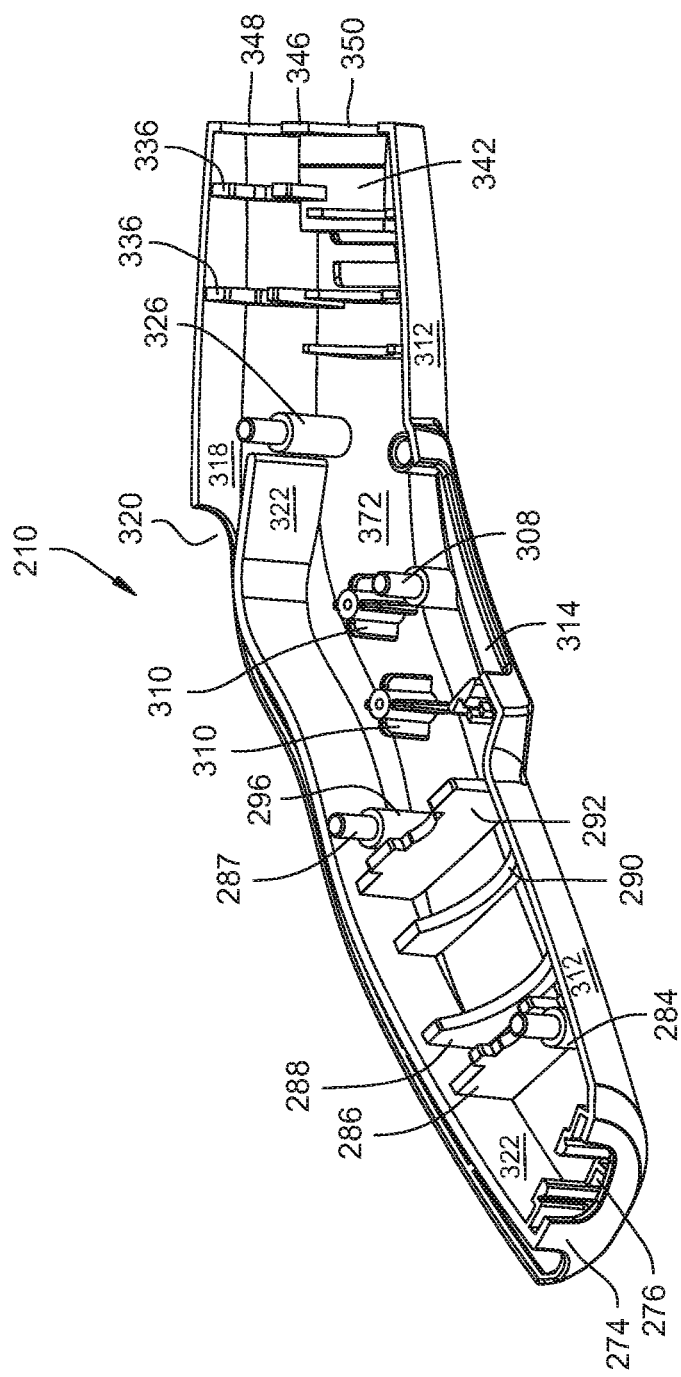
FIG. 8 is a perspective view of the left side shell.

From FIGS. 7 and 8 it can be seen that left shell 210 has a shape that is a mirror image of right shell 70. The left shell 210 has a base 272 and a set of rims that extend inwardly from the base. When shells 70 and 210 are placed together, the right shell rims 71, 139, 167 and 193 abut left shell rims 274, 312, 318 and 346, respectively.

The left shell 210 is formed so as to have a distal end rim, rim 274 that is formed with a notch 276. The left shell notch 276 is symmetric to the right shell notch 72. Here, the "symmetry" between shells 70 and 210 components is around a plane that extends top-to-bottom between the shells. The left shell is formed with two brackets, brackets 278 and 280 that are located proximally forward of and extend over notch 276. Bracket 278 is symmetric in location and shape to right shell bracket 74. Bracket 280 is symmetric in location and shape to right side bracket 78. Thus while not identified, bracket 278 can be considered to be formed to have a step 75 and a rib 76. Bracket 280 has a step 79 and a rib 80.

Four posts, posts 284, 296, 308 and 326 extend outwardly from the inner surface of shell base 272. Each post 284, 296, 308 and 320 is formed to have a pin 287 (only one identified) that extends outwardly from the free end of the post. Pins 286 have a diameter that is smaller than that of posts 284, 296, 308 and 326. Shells 70 and 210 are constructed so that when the shells are pressed together to assemble handpiece 64: the pin 287 integral with post 284 seats in the bore hole integral with right shell boss 86; the pin 287 integral with post 296 seats in the bore integral with right side boss 106; the pin 287 integral with post 308 seats in the bore integral with boss 155; and the pin 287 integral with post 326 seats in the bore integral with boss 162. The shell components are further dimensioned seating of the pins 287 in the complementary bosses serves to snap or compression fit the two shells 70 and 210 together.

Between posts 284 and 296, ribs 286, 288, 290 and 292 extend outwardly from the inner surface of shell base 212. Rib 284 is symmetric in shape and location to right side rib 88. Rib 284 is thus formed with tabs 90. Rib 288 is symmetric in shape and location to right side rib 92. Rib 290 is symmetric in shape and location to right side rib 96. Rib 292 is symmetric in shape and location to right side rib 102.

The left shell 210 is further formed so that forward of and below post 296 a bracket 298 extends outwardly from the inner surface of the shell base 212. Bracket 298 is symmetric with respect to right shell bracket 122. Accordingly, while not identified, it is understood that bracket 298 has the same surfaces 124, 126, 128, 130 132, 134 and 136 as bracket 122.

Two bosses 304 and 308 project outwardly from left side shell base 272. Boss 304 is symmetric in position to right shell boss 110. Boss 308 is symmetric in position to right side boss 150. Each boss 304 and 308 is formed with a closed end bore, (bores not identified). Reinforcing webs 306 extend outwardly from the perimeter of each boss 304 to the shell base 272.

Left shell 210 has a lower rim 312. The bottom rim 312 is formed with a notch 314 that is symmetric in shape and location to notch 140 integral with right shell 70. Immediately forward of notch 314, a boss 316 extends upwardly from left shell base 272. Boss 316 is symmetric with right shell boss 164. The boss 316 is formed with a closed end bore, (not identified).

Opposite lower rim 312, the left shell 210 has a top rim 318. The shell 210 is shaped so that a notch 320 extends distally forward from the proximal end of rim 318. Notch 320 is symmetric with respect to right shell notch 168. A ledge 322 projects outwardly from shell base 212 below notch 320. The left shell ledge 322 is symmetric with respect to the right shell ledge 170. The left shell 210 is further formed to have webs 324. Webs 324 are symmetric with respect to right shell webs 172. When handpiece 64 is assembled, irrigation tube 56 rests on ledge 322 and abuts webs 324.

Forward of post 326, the left shell 210 is formed with three parallel yokes 330, 332 and 334. Yoke 330 is symmetric in shape and location with respect to right shell yoke 176. Yoke 332 is symmetric in shape and location with respect to right side yoke 178. Yoke 334 is symmetric in shape and location with respect to right side yoke 180.

Located above yokes 332 and 334 are two additional parallel yokes, yokes 336. Each yoke 336 is symmetric in shape and location to a separate one of the right shell yokes 182. Yokes 336 extend outwardly from the inner surface of top rib 318.

Left shell 210 is formed with a through opening 340 and a recessed panel 342. Through opening 340 is symmetric and shape and location with respect to the through opening 186 integral with the right shell 70. Panel 342 is symmetric with respect to the right shell recessed panel 188. The left shell 210 has a distal rim, rim 346. Rim 346 is formed to have semi-circular two notches 348 and 350. Notch 348 is symmetric with respect to right shell notch 194. Notch 350 is symmetric with respect to left shell notch 196.

Returning to FIGS. 3 and 4, it is understood that motor 360 is sandwiched between shells 70 and 210. The motor has a main body 362 that has plural cylindrical sections of diameters that are similar in length. A cylindrical head 364 extends forward from body 362. A rotating shaft 366 extends forward from the head 364. Motor head 364 has a diameter less than that of the body 362. Shaft 366 has a diameter less than that of the motor head 364. The motor body 362 is seated against the notch-defining inwardly curved faces of right sleeve ribs 92 and 96 and the complementary faces of the left sleeve ribs 288 and 290. The proximal end of the body 362 is disposed against the distally directed face of shell ribs 88 and 286. The distal end of the motor body is disposed against the proximally directed faces of shell ribs 102 and 292. The motor head 364 extends through the notches defined by the shell ribs 102 and 292.

Figure 9:
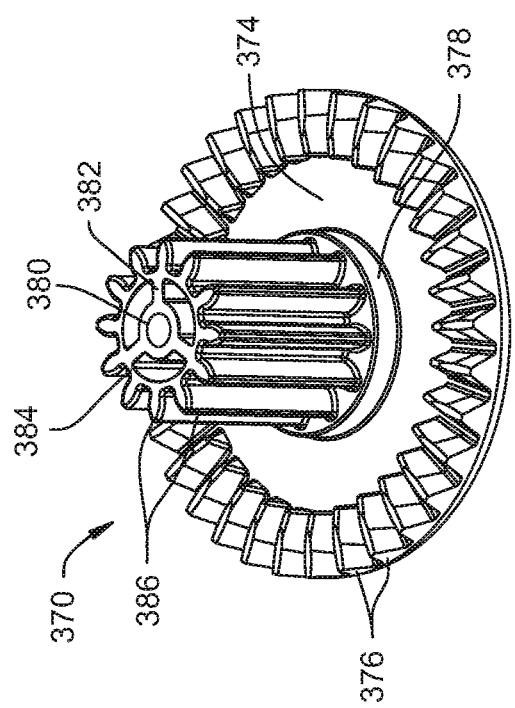
FIG. 9 is a perspective view of the face gear internal to the handpiece.
Figure 11:
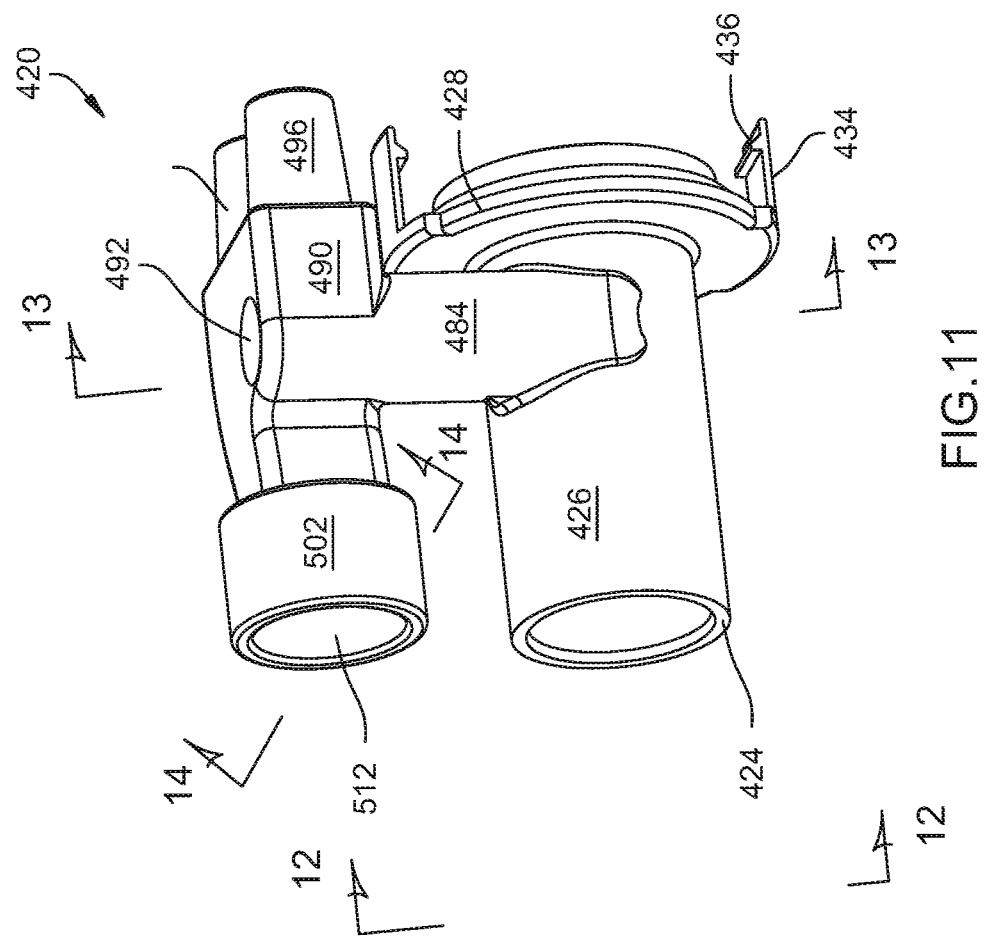
FIG. 11 is a perspective view of the pump housing internal to the handpiece.

A gear 370 is fitted to the free end of the motor shaft 366 to rotate with the shaft. Gear 370 engages a face gear 372 also internal to the handpiece 64. The face gear 372, as seen in FIG. 9, includes a disc shaped base 374. Teeth 376 extend upwardly from the base 374 so as to extend around the outer perimeter of the base. A raised circular pedestal 378 extends upwardly from the center of base 374. Inner and outer sleeves 380 and 384, respectively, extend upwardly from the exposed surface of pedestal 378. Pedestal 378 and sleeves 380 and 384 are coaxial with the center axis, the rotational axis of gear base 372. The inner surface of outer sleeve 384 is spaced radially outwardly away the inner sleeve 380. Arcuately spaced apart webs 382 extend between the outer surface of the inner sleeve 380 to the adjacent inner surface of the outer sleeve 384. Not identified is the coaxial through bore that extends through the inner sleeve 380 and the underlying pedestal 378. The outer sleeve is formed with teeth 386.

A pin 390, seen in FIG. 4, rotatably holds the face gear 370 in handpiece 64. Pin 390 extends through the axial bore through pedestal 378 and inner sleeve 380. One end of pin 390 is seated in the bore integral with right shell boss 110. The opposed end of pin 390 is seated in the bore integral with left shell boss 304. The face gear 370 is positioned so the gear base 372 is adjacent right shell boss 110. When handpiece 64 is assembled, shaft gear 370 engages face gear teeth 376.

Figure 10:
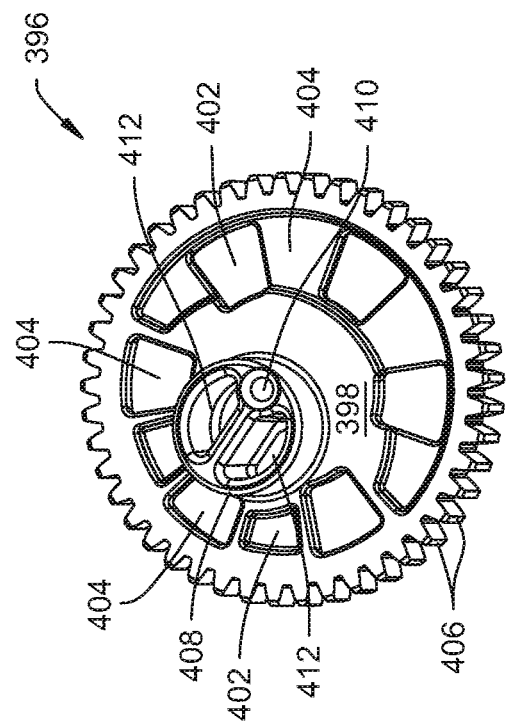
FIG. 10 is a perspective view of the eccentric gear internal to the handpiece.

The face gear 370 drives an eccentric gear 396 also rotatably disposed in the handpiece 64. The eccentric gear 396, seen best in FIG. 10, is formed with a circular base 398. The base 398 is formed with a number of arcuately spaced apart through openings 402. Base 398 is also formed to have a number of arcuately spaced apart recesses 404. The recesses 404 are located inwardly of the outer perimeter of the base. In the depicted version of the disclosure, the recesses subtend different arcs. Further, the recess 404 that extends the large arc intersects plural openings 402. Teeth 406 protrude outwardly from the outer perimeter of base 398. A cylindrical head 408 protrudes upwardly from gear base 398. The center longitudinal axis of the head 408 is laterally offset from the rotation axis of the base 398. The eccentric gear is further formed to have a through bore 410. Bore 410 extends through the rotational axis of the base and an outer portion of head 408 that extends over the rotational axis of the base 398. Gear 396 is formed with two voids 412. Voids 412 extend through the head 408 and the portion of the base 398 below the head. Voids 412 are symmetric around a plane that bisects bore 410.

A pin 416, seen in FIG. 4, rotatably holds the eccentric gear 396 in the handpiece 46. One end of pin 416 is seated in the bore integral with right shell boss 150. The opposed end of pin 416 seats in bore integral with left shell boss 308. When the handpiece 64 is assembled, eccentric gear teeth 406 engage teeth 386 of the face gear 372.

The pump 420 includes a pump housing 422 now described by reference to FIGS. 11-14. The pump housing 422 is formed from a single piece of molded plastic and includes a base 424. The base 424 includes an outer sleeve 426 that along the outer surface is of generally of constant diameter. A lip 428 protrudes radially outwardly from the proximal end of sleeve 426. A ring 430 extends proximally rearward from lip 428. Ring 430 is located inwardly of the outer perimeter of lip 428. In the depicted version of the disclosure, ring 430 has an inner diameter that is greater than the outer diameter of outer sleeve 426. Pump housing is further formed so that along the outer surface of the ring a step 432 extends circumferentially around the ring. The outer diameter of the proximal portion of the ring 430 is thus less than the outer diameter to the distal portion of the ring, the portion distal to step 432. Two flexible legs 434 extend rearwardly from lip 428. Legs 434 are diametrically opposed to each other. Each leg 434 is formed with an inwardly directed foot 436.

Pump housing 422 is formed with an inner sleeve 438 that is coaxial with and disposed in outer sleeve 426. Inner sleeve 438 extends distally from the proximal end of the outer sleeve 426. The inner sleeve 438 terminates at a location approximately at the mid plane through the outer sleeve. Not identified is the circular web internal to the outer sleeve that extends to the inner sleeve. Sleeves 426 and 438 are dimensioned that that there is an annular gap between the sleeves (gap not identified). At the proximal end of the inner sleeve 438 a circular lip 442 projects inwardly from the sleeve.

The outer sleeve 426 is further formed so that three bores collectively extend through the sleeve. A first bore, bore 446 is defined by the inner wall of the inner sleeve 438. A second bore, bore 480 is located immediately forward of bore 446. The third bore, bore 482 forms the distal end opening into the outer sleeve 426. The sleeve 426 is formed so that bore 482 has a diameter greater than that of bore 480.

Figure 13:
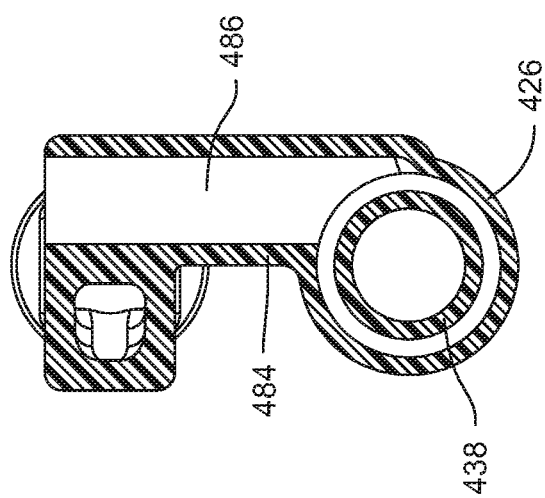
FIG. 13 is a cross section view of the neck of the pump housing taken along line 13-13 of FIG. 11.
Figure 12:
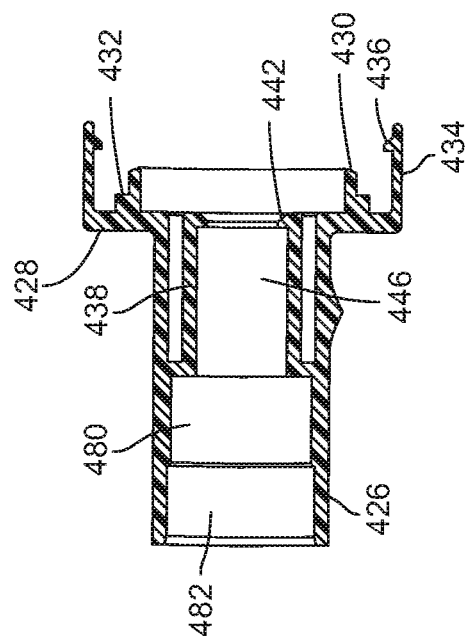
FIG. 12 is a cross sectional view of the bottom portion of the pump housing taken along line 12-12 of FIG. 11.
Figure 14:
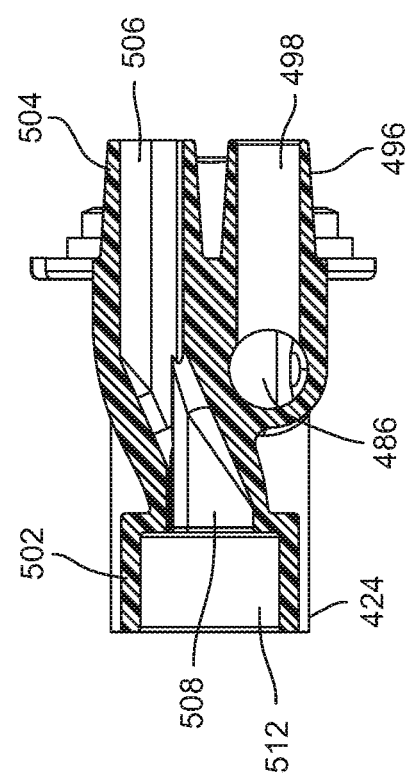
FIG. 14 is a cross sectional view of the head of the pump housing taken along line 14-14 of FIG. 11.

Pump housing 422 is further formed to have a cylindrical neck 484. Neck 484 extends perpendicularly upwardly from outer sleeve 426. The pump housing 484 is formed so that the neck 484 extends upwardly along an axis that, in addition to being perpendicular to the longitudinal axis through sleeve 426 is laterally offset from the longitudinal axis through sleeve 426. Neck 484 is formed with a channel 486. As seen in FIGS. 12 and 13, channel 486 opens into the annular gap between outer and inner sleeves 426 and 438.

Housing neck 484 extends to a head 490. Pump housing head 490 has a main section, not identified, that is formed from a number of subs-section that can generally be considered polygonal in shape. In the disclosed version of the disclosure, the head 490 is formed with a top located opening 492. The opening 492 is coaxial with neck channel 486. Opening 492 is present as a result of the injection molding process used to form pump housing 422. More specifically, the opening 492 is present as a result of the component of the mold that defines neck channel 486. During the process of manufacturing handpiece 64 a cap 494 seen only in FIG. 4, is fitted on the top of housing head 490 to close opening 492.

The pump housing 422 is formed so that two fittings, fittings 496 and 504, extend proximally from the proximally directed face of the head 490. Fitting 496 is the fitting to which the distal end of irrigation tube 56 is fitted. The housing 422 is formed with a closed end bore 498 that extends through fitting 496 partially through the head 490 to the neck channel 486. The bore 498 thus is the conduit through which the irrigating fluid flows from the irrigation tube into the pump housing base 424.

A cylindrical nose 502 extends distally forward from the housing head 490. Nose 502 is formed with a cylindrical bore 512 that extends proximally rearward from the distal front end of the nose. Nose 502 and bore 512 share a common longitudinal axis. An extension of this axis would extend through the housing head 490 between where the fittings 496 and 504 extend from the head. Two channels 506 and 508 function as the fluid communication path through the head from fitting 502 to bore 512. Channels 506 and 508 are along axes that are planar. A first one of the channels, channel 506, extends distally forward through fitting 504 and the proximal portion of the head. Channel 508 extends proximally from the base of bore 508 into the distal portion of head 490. Both channels 506 and 508 have D-shaped cross sectional profiles. Channels 506 and 508 are not coaxial. Instead, pump housing 422 is formed so that widest portion of channel 506 is in registration with the widest portion of channel 508. The housing head is further formed so that the most distal portion of channel 506 tapers into channel 508. Similarly, the most proximal portion of channel 508 tapers into channel 506. Thus, channels 506 and 508 collectively form a non-linear path through pump housing 422.

Upon assembly of handpiece 64, the pump housing base 424 is sandwiched between right shell yokes 176, 178 and 180 and complementary left shell yokes 330, 332 and 334. The distally directed surface of housing lip 428 is disposed against the proximally directed surfaces of yokes 178 and 320. Pump housing head 490 is seated in the notches integral to right shell yokes 182 and the notches defined by the complementary left shell yokes 336.

A bellows 514, seen best in FIGS. 15 and 16, also part of pump 420, extends proximally from the housing base 424. Bellows 514 is formed from a flexible thermoplastic and has a cylindrical main body 516 formed with circumferentially extending pleats (not identified). Bellows body 516 has a proximal closed end. A button 519 extends outwardly from the closed end of bellows body 516. A neck 517, that has a diameter less than that of button 519, connects the button to the closed end of the body 516. A lip 518 extends radially outwardly and circumferentially around the open end of bellows body 516. A ring 520 extends from the outer perimeter of lip 518 towards housing ring 430. More particularly, bellows ring 520 extends snuggly around housing ring 430. An O-ring 524, seen only in FIG. 15, is seated on the step 432 integral with ring 430. The O-ring 524 is pressed between the housing ring 430 and bellows lip 518. The O-ring 524 contributes to the seal between the bellows 514 and pump housing base 424. The housing legs 434 extend over the outer surfaces of bellows ring 520. The housing feet 436 extend over the bellows lip 518 so as to hold the bellows to the pump housing 424.

A duck billed valve 526, also part of pump 420, is seated in the bore defined by housing bore 446. Valve 526 is arranged so that the open end of the valve is directed towards the bellows 520. The lips of the valve 526 are directed towards tube bore 480. Valve 526 has a base 528 that extends radially outwardly from the valve around the open end of the valve. Base 528 is curved in cross section. The outer perimeter of the valve base 528 extends over the proximal end of the inner sleeve 438 and the adjacent lip 442.

When handpiece 64 is assembled, bellows lip 516 is disposed against the distal facing surfaces of yokes 176 and 330. This component contact prevents the proximal movement of both the pump housing 420 and the bellows lip 516.

Figure 17:
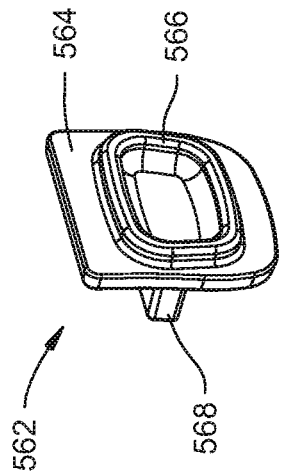
FIG. 17 is a perspective view of the pump yoke internal to the handpiece.

A yoke 534, also part of pump 420, is moveably disposed in handpiece 64. As seen best in FIG. 17, yoke 534, which is a single piece unit, includes a generally rectangular frame 536. The longitudinal axis of the frame 536 is parallel with the longitudinal axis of the handpiece barrel. Frame 536 is formed from a number of longitudinally and lateral extending beams 538 and 540, respectively. The two most proximally located lateral beams 540 are curved so as to define an oval opening 542 in the frame. The major axis opening 542 is perpendicular to the longitudinal axis major axis of the frame 536. Open 542 has a minor width that is dimensioned to receive eccentric gear head 406.

Yoke 538 further includes two parallel disks 544 and 546 that are located at the distal end of frame 536. Disks 544 and 546, which are spaced apart from each other, are located in planes perpendicular to the plane of yoke frame 536. The disks are centered on an extension of the longitudinal axis through the frame. The distalmost disk, disk 546 is formed with a U-shaped notch 550. The center of the base of notch 546 is located on the extension of the longitudinal axis through the frame. Disks 544 and 546 are spaced apart distance that facilitates the snug fitting of bellows button 519 between the disks. Disk 546 is shaped so that notch 550 can receive bellows neck 517.

Upon assembly of handpiece 64, the yoke 534 is positioned to seat on right shell rails 142, 148, and 152. More particularly the yoke 534 is disposed between rim 144 of rail 142 and rim 153 of rail 152. When the yoke 534 is so positioned, head 408 of eccentric gear 396 seats in the yoke frame opening 542. The bellows button 519 *s* is seated between disks 544 and 546. Owing to the construction of both the bellows 514 and the yoke 534, the bellows body 516 expands and contracts with the reciprocation of the yoke.

Figure 18:
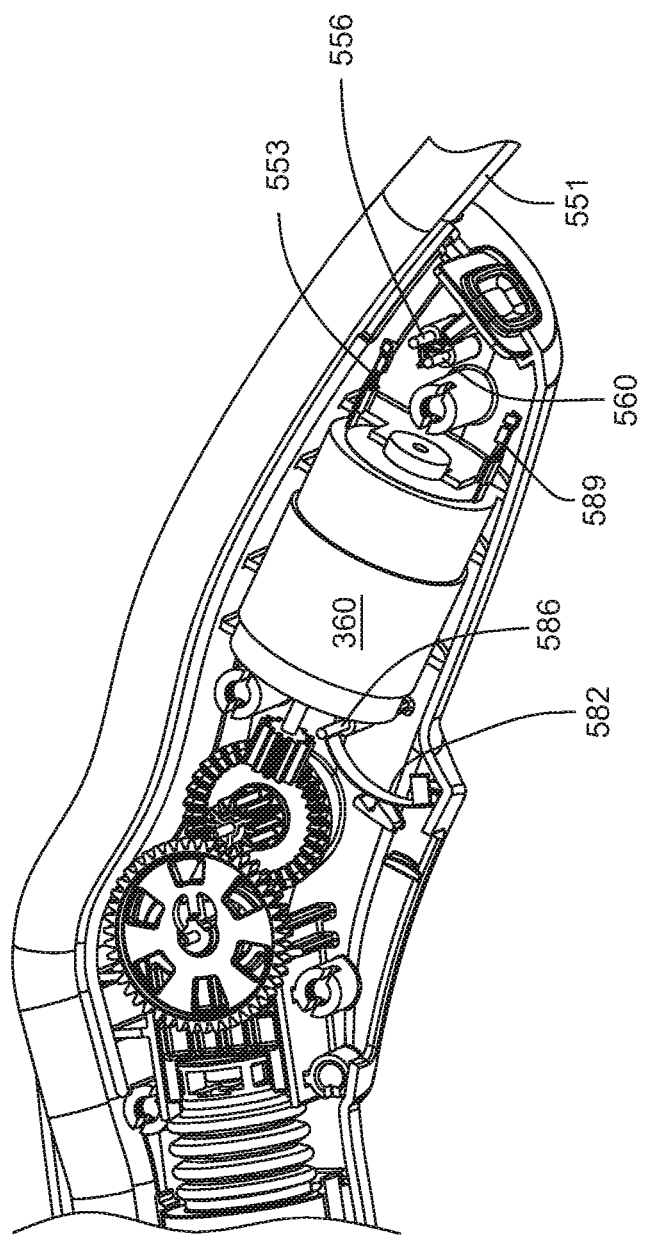
FIG. 18 depicts the conductive components internal to the handpiece.

A cable 551 seen in FIG. 18 and in dashed lines in FIG. 18A, is typically bundled with the assembly that comprises the paired irrigation tube 56 and suction tube 66. The proximal end of the cable is connected to a power supply 549 associated with the lavage unit 50. This power supply 549 may take the form of a battery pack. Alternatively, the power supply may take the form of a device that converts AC voltage into DC voltages that are two different potentials. The exact structure of the power supply is not a part of the structure of the lavage unit 50 of this application. In FIG. 18A the power supply 549 is depicted as four series connected cells (individual cells not identified).

Internal to the cable 551 are plural insulated wires. For ease of illustration, these wires are only shown in FIG. 18A. One wire, wire 552, is connected to a contact 553 attached to motor 360. The proximal end of wire 552 is typically connected to the ground associated with the power supply 549. Cable 550 includes two additional wires, wires 554 and 558. Wires 554 and 558 are the wires over which energization signals having different potentials are sourced from the power supply 549 to the handpiece. In FIG. 18A this is depicted by wires 552 and 554 being collectively connected to all four cells and wires 552 and 558 being collectively connected to only two cells. Wire 554 is connected to a conductive post 556 that projects from a first one of the right shell bosses 84. Wire 558 is connected to a conductive post 560 that projects from the second right shell boss 84.

Figure 19:
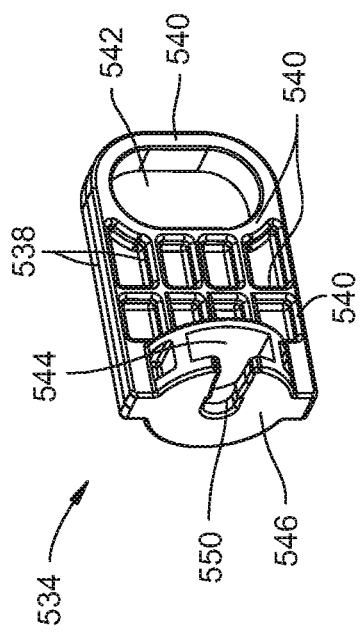
FIG. 19 is a perspective view of the exposed portions of the handpiece speed control switch.
Figure 20:
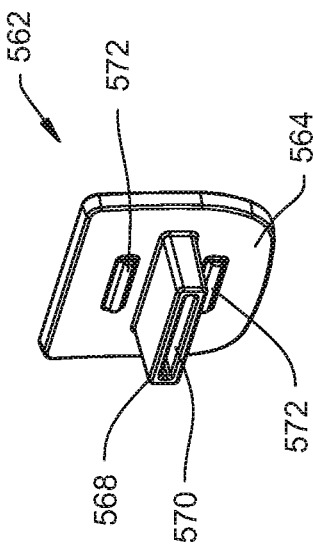
FIG. 20 a perspective view of the concealed features of the speed control switch.

The switch 562 is slidably mounted to the proximal end of handpiece 64. Switch 562, now described with respect to FIGS. 19 and 20, includes a plate 564 that is generally rectangularly shaped. A closed loop rib 566 protrudes outwardly from the proximally directed surface of plate 564. Rib 566 is generally in the form of a rectangle with rounded corners. The rib 566 is dimensioned to define a space, (not identified,) for receiving the tip of thumb or finger. An elongated foot 568 extends perpendicularly forward from the distally directed surface of plate 564. Foot 568 is generally triangularly shaped. The switch 562 is formed so to have a void space 570 that extends inwardly from the distal end of foot 568. Two parallel ribs 572 also project outwardly from the distally directed face of plate 564. Ribs 572, in addition to being parallel to each other, are parallel to the plane in which foot 568 is disposed. A conductive contact 576 is seated in and extends outwardly from foot void space 570.

Switch 562 is mounted to the handpiece so that the proximally directed face of plate 564 is disposed against the inner surfaces of shells 70 and 210. The proximally directed face of switch plate 564 is accessible through the opening in the handpiece formed by the contiguous notches 72 and 276. The distally directed face of plate 564 is located immediately rearward of right side shell brackets 74 and 78 and the complementary left shell brackets 278 and 280.

Switch 562 slidably moves within the space in which the switch is mounted. Switch 562 is held in one position by the abutment of the lower located rib 572 against the lower surface of complementary handpiece ribs 76. The switch is held in the second position by the abutment of the upper located rib 572 against the top surface of rib 80. Owing to the flexible nature of brackets 74 and 278 and brackets 78 and 280, manual force can flex the brackets and associated ribs so as to allow the sliding movement of switch 562. Contact 576 is disposed between conductive posts 556 and 560. Depending on the position of switch 562, the contact 576 abuts either post 556 or post 560.

An insulated wire 578 extends from contact 576. The terminal 577 that connects wire 578 to connector 576 is seen in FIG. 4. This terminal 577 is connected to a tab (not identified) that is part of contact 576. The opposed end of wire 578 is connected to a contact 582 moveably mounted to right shell 70. Contact 582, best seen in FIG. 18B, is the form of an arcuately shaped flexible piece of metal. At one end contact 582 has a curved head 584 the head of the contact seats in the void space between tab 143 and the shell lower rim 139. In FIG. 18, trigger 561 is not seen so the position of the contact relative to right side shell 70 can be better seen. Adjacent head 584, the contact has a tab 585. Tab 585 is the structural component of the contact to which a connector 587 (FIG. 4) is attached. The connector 587 is the component that holds the end of wire 578 to contact 582.

The body of contact 582 curves first distally away from the head. The free end of the contact 582 curves upwardly and proximally towards the distally directed face of the motor 360. The free end of the contact 582 is positioned to abut a conductive post 586 that projects upwardly from boss 108. Owing to the shape of the contact and the restraining force of tab 143, contact 582 is normally spaced from post 586. An insulated wire 588 extends from post 586 to the second connector 589 attached to motor 360.

When handpiece 64 is assembled, contact 582 is positioned so that the contact head 584 seats around shell pin 135. The body of the contact 582 extends distally away from the pin in the space adjacent the distal end of shell bracket 137.

Figure 21:
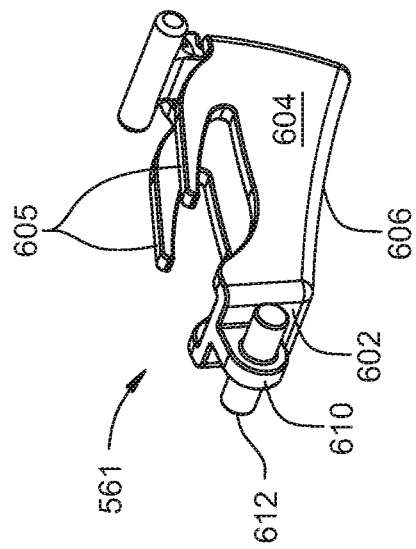
FIG. 21 is a front perspective view of the trigger.
Figure 22:
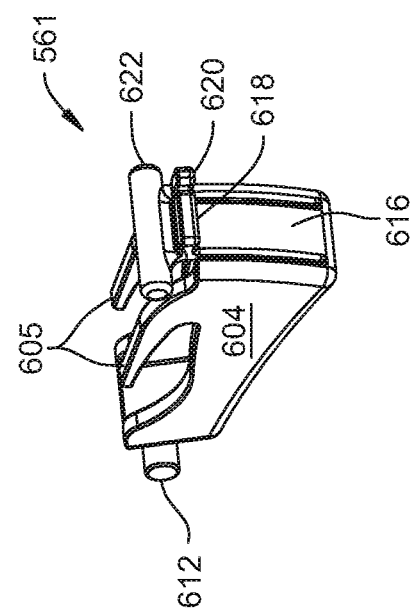
FIG. 22 is a rear perspective view of the trigger.

The trigger 561, as seen best in FIGS. 21 and 22, is formed from a single piece of plastic. The trigger 561 is shaped to have a front panel 602 that is generally rectangular in shape. Two parallel side panels 604 extend proximally rearward from the oppose side edges of the front panel 602. The side panels 604, in addition to extending proximally curve downwardly below the front panel 602. A finger 605 protrudes forward from the proximal end of each side panel 604. Each finger 605 has a main body that is spaced above the side panel 604 with which the finger is integral. Each finger 605 is able to flex and return to its initial position relative to the associated side panel 604. A bottom panel 606, only the edges of which are seen in the Figures, extends rearwardly from the front panel 602 and between the side panels 604. A tab 610 extends distally and perpendicularly from the front panel 602. Tab 610 is located in a plane that intersects the top to bottom longitudinal axis through the front panel 602. A cylindrical beam 612 extends through tab 610. The longitudinal axis of beam 612 is thus parallel to the lateral axis that extends side to side through the front panel 602.

A rectangularly shaped tab 616 extends upwardly from the proximal end edge of the bottom panel 606. Tab 616 is located between and spaced apart from the surrounding side panels 604. The tab 616 is able to flex relative to the rest of the trigger 561. A bar 618 extends laterally across the top of the tab 616. The bar 618 projects outwardly from the proximally directed face of the tab 616. In the depicted version of the trigger a small tab 620 is shown adjacent the bar protruding outwardly from one of the side panels 604. The trigger 561 is shaped so that tab 616 extends a short distance above the adjacent side panels. A cylindrical beam 622 extends across the top of tab 616. Beam 622 has a radius that facilitates the seating of the tab in the notch defined side surfaces 128 and step surfaces 130 of shell brackets 122 and 296.

Upon assembly of handpiece 64, the opposed ends of trigger beam 612 seat in the opposed bores formed in right shell boss 164 and left shell boss 316. The trigger 561 extends through the opening formed by contiguous notches 140 and 314. The trigger 561 is able to pivot around the longitudinal axis through beam 612. Downward movement of the trigger 561 is limited by the abutment of bar 616 against the inner surfaces of shell bottom rims 139 and 312 that define the proximal ends of notches 140 and 314.

Upward movement of the trigger 461 is limited by the abutment of fingers 605 against the interlocked boss 155 and post 308.

III. Tip Assembly

Figure 23:
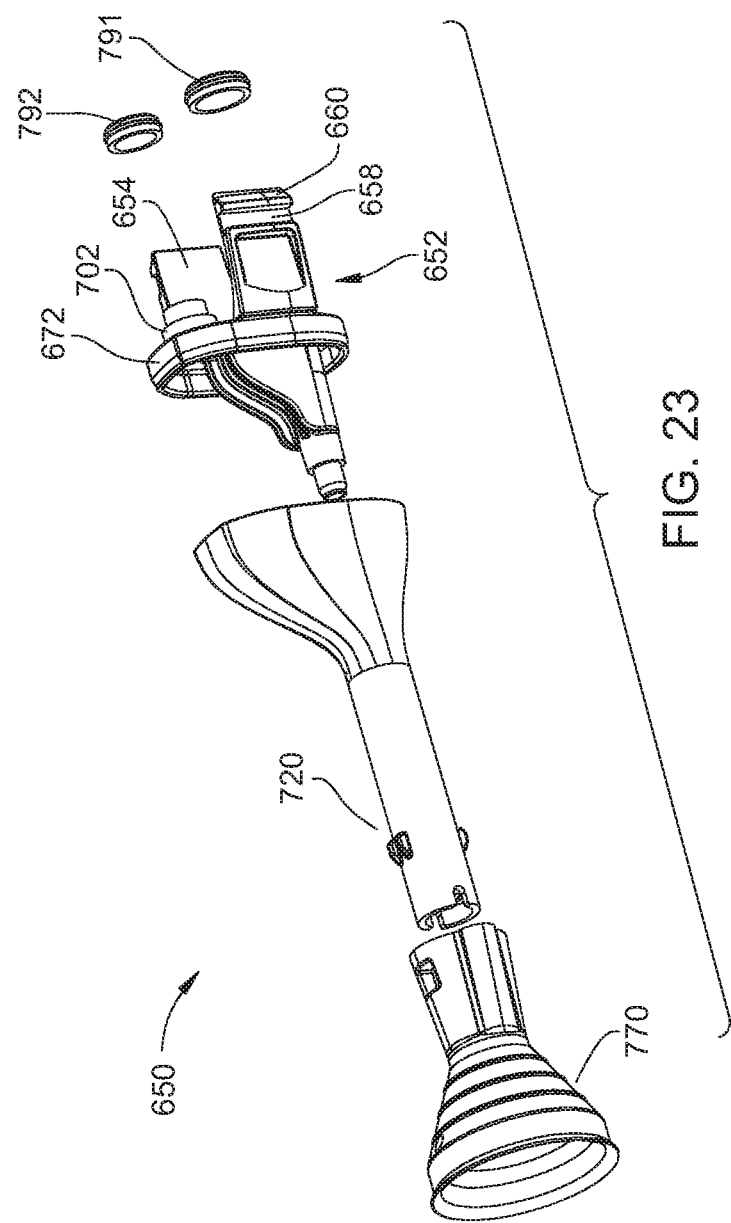
FIG. 23 is an exploded perspective view of the components forming the tip assembly of this disclosure.

The tip assembly 650 as seen in FIG. 23, includes a connector 652, a body 720 and the spray shield 770. Connector 652 is the component of the tip assembly that is removably attached to the handpiece 64. The body 720 includes the irrigation tube 730 through which the fluid discharged by the pump is discharged and the surrounding suction tube 750. The spray shield 770 is removably attached over the distal end of the body 720.

Figure 25:
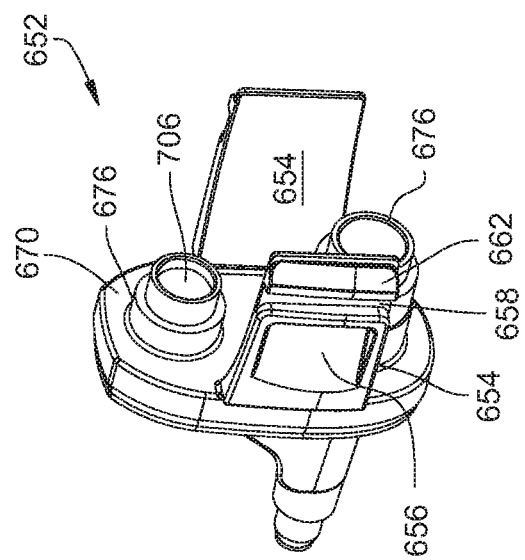
FIG. 25 is a perspective view of the rear of the connector.
Figure 24:
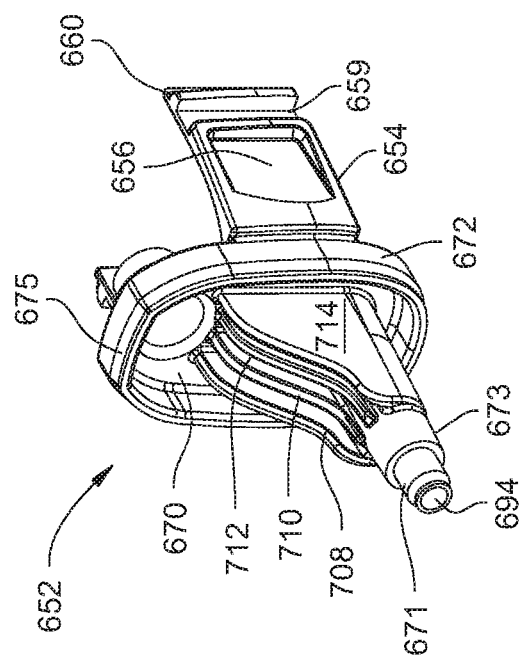
FIG. 24 is perspective view of the front of the connector of the tip assembly.
Figure 26:
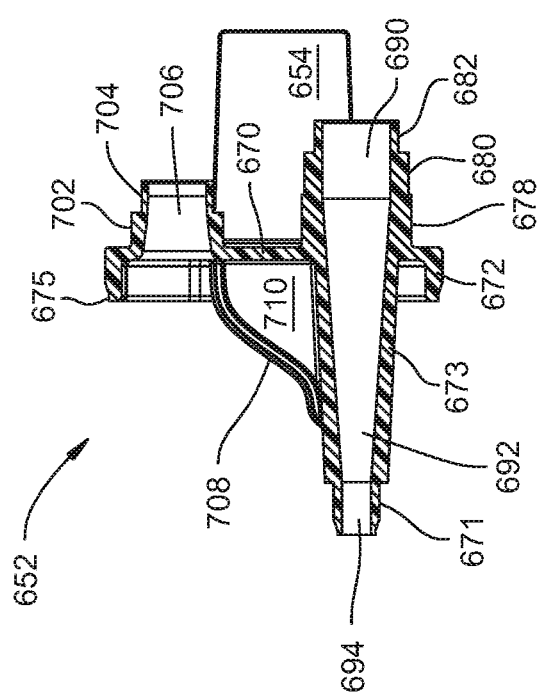
FIG. 26 is cross sectional view of the connector.

From FIGS. 24-26 it can be seen that connector 652 is formed from a single piece of plastic and is shaped to have a plate 670 that is approximately oval is shape. A leg 654 extends reward from each opposed sides, the opposed major side edges of the plate. Each leg 654 is generally in the form of a rectangular panel. The legs 654 are flexible relative to plate 670. Each leg 654 is formed to have a raised a recess 656 that extends inwardly from the outer exposed face of the leg. The recesses 656 are dimensioned to receive the tip of the finger. A foot 660 extends outwardly from the exposed face each leg. Each foot 660 is spaced from the recess 656 forming portion of the leg by a gap 658. Gaps 658 have a proximal-to-distal width that accommodate the seating of the portions of the shell bases 69 and 272 that extend between openings 186 and 338 and the complementary recessed panels 188 and 342. The feet 660 extend laterally, top to bottom, along legs 654. Each foot 660 has at the proximal end of the foot, a surface 662 that tapers outwardly and distally forward away from the leg 654 with which the foot is formed.

A rim 672 extends distally forward around the outer perimeter of the connector plate 670. The connector 652 is further formed so that rim 672 has a recessed surface 675 that at the distal front end of rim is located inwardly from the rest of the rim The rim 672 is formed so that recessed surface 675 extends circumferentially around the rim.

The connector 652 is further formed so that a tube like irrigation fitting 676 extends through the plate 670. Irrigation fitting has three sections each with a constant outer diameter that are located proximal to the plate. A first section, section 678, is located immediately adjacent the plate 670. A second section, section, 680 extends proximally from section 680. A third section, section 682 extends proximally from section 680 and is the most proximal portion of irrigation fitting 676. Section 680 has an outer diameter less than the outer diameter of section 678. Section 682 has an outer diameter less than the outer diameter of section 680. section Irrigation fitting has an elongate section, section 673 that extends forward of the plate 670 and is coaxial with sections 676, 678 and 680. Section 673 has an outer diameter that extending distally from the plate 670, decreases. A nose 684 forms the most distal portion of the irrigation fitting 676. Nose 684 has an outer diameter less that of the adjacent section 682. The most distal end of the nose is tapered such that extending proximally from the distal end of the nose the outer diameter of the distal end portion increases. The connector 652 is further formed so that three concentric bores 690, 692 and 694 extend through the irrigation fitting. Bore 690 extends distally from the proximal end of fitting section 680 to approximately where fitting sections 676 and 678 meet. Bore 690 is of constant diameter. Bore 692 extends from the distal end of bore 690 through fitting sections 678 and 673. The diameter of bore 692 decreases with distance from bore 690. Bore 694 begins at approximately the location where nose 682 emerges from fitting section 682. Bore 694 is of constant diameter and extends to the distal end of the irrigation fitting 676.

Connector plate 670 is also formed to have a generally tubular suction fitting 702 that extends proximally rearward from the plate so as to rearward of rim 672. Suction fitting 702 has a proximal most head section 704. The head section 704 has an outer diameter less than that of the main body of the fitting 702 (main body not identified). A bore 706 extends axially through the suction fitting 602. The connector 652 is formed so that as the bore extends proximally from the opening in plate 670 there is a decrease in the diameter of the bore.

The connector 652 is further formed so that four parallel spaced apart ribs 708, 710, 712 and 714 extend upwardly from the elongate section 682 of the irrigation fitting 676. Ribs 708 and 714 extend outwardly from the opposed outer sides of section 682. Ribs 710 and 712 are located between ribs 708 and 714 Ribs 710 and 712 extend upwardly from the top surface of fitting section 682. Each 708, 710, 1712 and 714 terminates at a location adjacent where bore 706 starts to taper inwardly from distally directed face of plate 706. The ribs 708, 710, 712 and 714 each have a top surface (surfaces not identified) that from the distal end of the irrigation fitting elongate section 682 curves in a concave shape upwardly and proximally, then tapers linearly upwardly and the curves in a convex shape to the plate 670. The ribs are formed so that the top surfaces of ribs 708 and 714 are located above the top surfaces of ribs 710 and 712.

Figure 27:
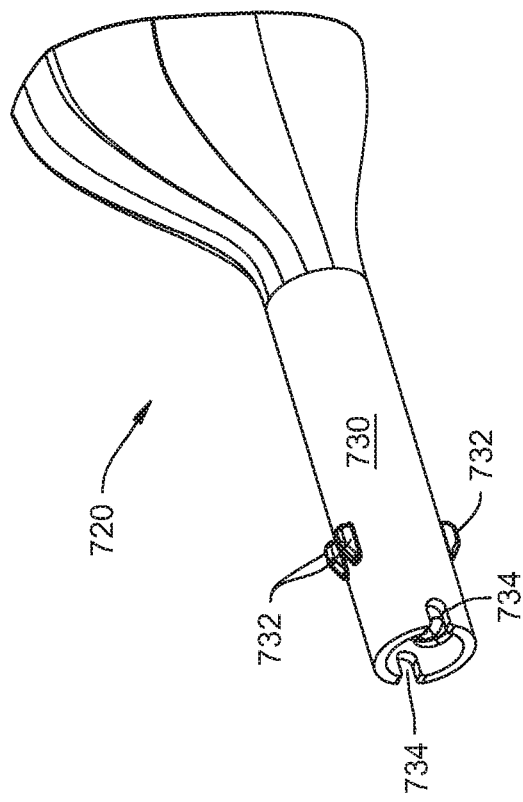
FIG. 27 is a perspective view of the body of the tip assembly.
Figure 29:
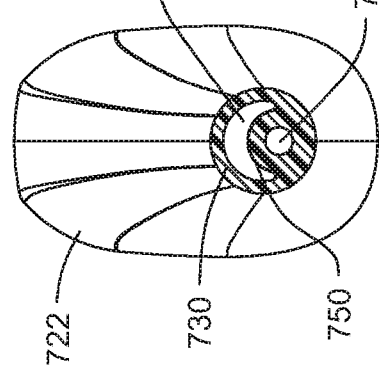
FIG. 29 is a cross sectional view of the body of the tip assembly taken along line 29-29 of FIG. 28.

The tip assembly body 720, now described by reference to FIGS. 27-29, is formed as a single-piece unit. The body is shaped to have head 722. The head 722 has an oval shaped lip 724. Lip 724 is dimensioned to fit snuggly over the rim 672 integral with connector 652. Not identified are the outwardly stepped surfaces formed in the inner wall of lip against which rim 672 and the distally located recessed surface 675 of the rim seat. The head 722 defines a void space 725 located forward of lip. The head 722 is asymmetrically shaped in that the outer surface of the head, adjacent the top of lip 724 tapers to a location offset from the minor axis running through center of the opening defined by the lip. More particularly the head defines a void space 725 dimensioned to extend a short distance distally relative to where bore 706 extends from plate 652 and a longer distance distally so as to accommodate the elongate section 582 of the irrigation fitting 676. Thus, the head 720 is shaped so that the cross sectional area of the head, in planes perpendicular to the longitudinal proximal-to-distal axis along tip assembly body 720, decreases as the head extends distally forward.

Suction tube 730 has constant inner and outer diameters and extends distally forward from the distal end of head 722. Approximately 2 cm from the distal end of the tube, suction tube 730 is formed to have four tabs 732, (only three seen in FIG. 27,) that project outwardly from the outer surface of the tube. Two tabs 732 are parallel with each other and extend outwardly from the tube adjacent the top of the tube 730. The remaining two tabs 732 are symmetrically located with respect to the first two tabs relative to a plane that extends through the longitudinal axis that extends between the proximal and distal ends of the tube 730.

The suction tube 730 is further formed to have two notches 734 that extend inwardly from distal end of the tube. Notches 734 are U-shaped. The notches 734 are symmetrically located and around a longitudinal axis that extends between the proximal and distal ends of the tube. If tabs 732 are considered extending from the top and bottom portions of the suction tube 730, notches 734 extend inwardly from the opposed sides of the tube.

Irrigation tube 750 is disposed inside suction tube 730. The irrigation tube 750 is not coaxial with the suction tube 730. Instead, the irrigation tube 750, which has an outer diameter less than that of the inner diameter of the suction tube 730, extends outwardly from the inner wall of the suction tube 730. Thus, owing to the position of the irrigation tube in the suction tube, the suction tube can be considered to have a through lumen 736 that, as seen in FIG. 29, is crescent shaped. Tip assembly body 720 is further formed so that the irrigation tube 750 terminates at a location proximal to the distal end of the suction tube 750.

The irrigation tube 750 is formed to have a number of contiguous coaxial bores. A first bore, bore 752 extends forward from the proximal end of the tube 750. Bore 752 is of constant diameter. A bore 754 is located immediately in front of bore 752. Bore 754 tapers inwardly as it extends distally. Bores 752 and 754 are collectively designed to receive and compression hold in place the nose 684 integral with the connector irrigation fitting 676. Forward of bore 754 tube 750 has a bore 756 of constant diameter. In terms of length, bore 756 is the shortest in length of the bores that extend through the irrigation tube 750. A bore 758 extends from the distal end of bore 756 to the distal end of the irrigation tube 750. Bore 758 is the longest in length and smallest in diameter of the bores forming the flow through path through the irrigation tube 750.

In the depicted version of the disclosure, a rim 760 extends inwardly and circumferentially around the distal end of the discharge tube. The rim defines an orifice 762 that extends forward from the distal end of bore 758. Rim 760 is dimensioned so that the diameter of the orifice increases distally from the distal end of bore 758.

Figure 32:
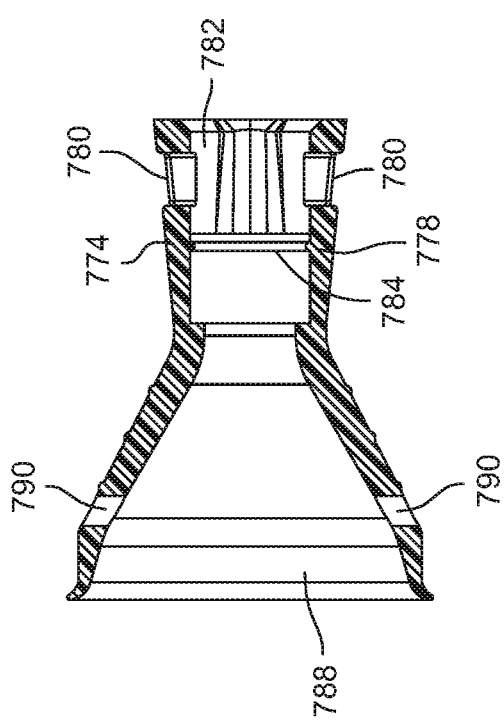
FIG. 32 is a cross sectional view of the spray shield taken along a plane that extends longitudinally through the spray shield.

The spray shield 770, now described with reference to FIGS. 30, 31 and 32, is formed from a single piece of flexible plastic such as PVC. The spray shield 770 is shaped to have a stem 772. Stem 772 is formed from four arcuate sections 774, 776, 778 and 780 that collectively defining an opening (not indentified) into which the distal end of the tip assembly body 720 is inserted. In FIG. 30, sections 774 and 778 are shown as forming the opposed top and bottom sections of the stem 772. The inner surfaces of sections 774 and 778 extend around portions of a circle that is approximately 1 mm smaller in diameter than the diameter of the distal end of irrigation tube 730. Sections 774 and 778 are shown as being each formed with a rectangularly shaped through opening 780. Through openings 780 are positioned and shaped to receive tip assembly body tabs 732. Stem sections 776 and 780 are located between stem sections 774 and 778. The stem section project outwardly beyond the circle defined by the outer surfaces of stem sections 774 and 778.

Spray shield 770 is further formed to have a head 786 that extends forward from the distal end of the stem 772. Head 784 has a conic shape such that the outer diameter of the head increases distally from stem 772.

Both the stem 772 and head 786 have internal void spaces. Void space 782 is the void space that extends axially from the proximal end of the stem 772 into the head. The spray shield 770 is further formed so that a rib 784 protrudes inwardly from the inner wall of the shield that defines void space 782. Head 786 has void space 788 that is generally conical in shape. The distal end of void space 788 defines the distal end opening into the spray shield 770. The spray shield 770 is further formed so that the head 786 has two bleed ports 790 that extend from the outer surface of the head into void space 788.

When tip assembly 650 of this disclosure is assembled, connector 652 is press fit in tube body head 722. A gasket 791, seen in FIG. 23, is disposed around the step between sections 680 and 682 of the assembly irrigation fitting 676. A gasket 792 is disposed around the step between the head 702 and main body of the suction fitting 702.

IV. Operation

Lavage unit 30 of this disclosure is prepared for use by first fitting the tip assembly 650 to the handpiece 64. This connection is performed by sliding the connector legs 654 over the outer surfaces of the recessed panels 188 and 342 integral with the handpiece 64. Each connector foot 660 seats in a separate one of the handpiece openings 188 and 338. The seating of feet 660 in the handpiece openings 188 and 338 releasably holds the tip assembly 650 to the handpiece. There is a small gap between the handpiece panels 188 and 342 and the connector legs 654. This gap allows the legs 654 to be flexed inwardly. The flexing of the legs inwardly retracts the connector feet 660 out of the handpiece openings 188 and 338. Once the connector feet 660 are so retracted, the tip assembly 650 can be removed from the handpiece 64.

As a consequence of the fitting of the tip assembly 650 to the handpiece, the connector irrigation fitting section 680 seats in bore 482 internal to the pump housing 420. Connector irrigation fitting 702 seats in pump housing bore 512.

The irrigation tube 56 is connected to the source of irrigating fluid 54. Suction tube 66 is connected to waste collection container 68 and suction source 61. The cable 550 is connected to the power supply. With these connections made, the lavage unit is ready for use.

When trigger 561 is not being depressed, owing to its shape, contact 582 is normally spaced from post 586. Consequently there is no current flow to motor 360. Pump 420 is therefore in the off state. The practitioner actuates the pump 420 by depressing trigger 561. This causes bar 618 to pivot upwardly so as to abut contact 582. The abutment of the bar 618 against the contact 582 results in the contact being pivoted against post 586. The abutment of contact 582 against post 586 closes the power circuit to the motor 360. The actuation of the motor 360 results in gears 370 and 396 and yoke 534 cooperating to reciprocate bellows 514. The expansion of the bellow 514 draws irrigating fluid from tube 56 through pump housing fitting 498 and channel 486 into the bellows. The retraction of the bellows forces the fluid out through valve 526 into the tip assembly irrigation tube 750. The fluid is discharged to the site at which the open end of the spray shield 720 is applied.

When contact 582 is pivoted into the above state, the body of the contact adjacent the contact head 484 presses against the adjacent end surface of beam 137. As a consequence of the continued pivoting of the contact, the material forming the beam stores potential energy that, when released, would cause the beam 582 to flex back into the off position wherein the beam is spaced from post 586.

When trigger 561 is initially displaced to actuate the pump 420, the trigger beam 622 travels over the proximally directed surfaces of handpiece brackets 122 and 298. This results in the trigger tab 616 flexing rearwardly from the side panels 604. Simultaneously the trigger fingers 605 press against boss 155 and complementary post 308 internal to the handpiece. Thus results in current flow to the 360 and the actuation of 424. As the trigger bar 618 moves contact 582 against post 586, the opposed end of the trigger beam seat in the notch defining side surfaces 128 of the brackets 122 and 298. When the trigger 561 is in this position, the resilient force of the fingers 605 abutment against boss 155 and post 308 can urge the trigger downwardly. Thus, if the practitioner wants to deactivate the pump 420 it is only necessary to release the force on the trigger 561. The restoring force imposed by the trigger fingers 605 on the rest of the trigger move the trigger downwardly. The bar 618 moves away from the contact 582. Owing to the resilient nature of the material forming the contact 582, the potential energy stored in the contact as a consequence of the flexing of the contact is released. This results in the contact 582 flexing away from post 586. This breaks the connection to the motor 360 so as to deactivate the pump 420. Thus the practitioner is able to, by the selective pivoting of the trigger 561, operate the lavage unit 30 in a momentary on/momentary off mode.

There may be a point in the procedure in which the practitioner wants the lavage unit 30 to continually discharge irrigating fluid. If the practitioner wants to operate the unit 30 in a constant on state, the practitioner pivots the trigger upwardly from the position of the momentary on state. This results in the trigger beam 622 seating against the step surfaces 130 of the brackets 122 and 298. Once the beam 622 is so positioned, the downward movement the fingers 605 impose on the trigger is blocked by the abutment of the beam against the bracket step surfaces 130. The practitioner can release the pivot force on the trigger and the trigger will stay in this position. Again when in this position, the trigger holds the contact 582 against the conductive post 586. Thus, when the trigger 561 is in this position the lavage unit is in a constant on state. The practitioner applies irrigating fluid without having to be take the mental and physical steps to ensure that the trigger is depressed.

Lavage unit 30 is transitioned from the constant on state to the off state by the continued depression of the trigger 561. This displacement of the trigger causes the opposed ends of the beam 622 to first travel over bracket side surfaces 132. Once the beam 622 reaches the top of side surfaces 132, the trigger tab 616 is free to flex distally to the static position of the tab. Beam 622 travels over bracket top surfaces 134. The biasing force imposed by fingers 606 is not opposed. The force imposed by fingers 606 move the trigger downwardly. During the initial part of this downward movement of the trigger 561, beam 622 travel over the distally directed side surfaces 136 of the brackets 122 and 298. As a consequence of the forward and downward movement of the trigger beam 622, the beam moves away from contact 582. Owing to the resilient properties of the material from which the contact 582 is formed, the contact returns to its initial static state in which the contact is spaced from the post 586. Again, the movement of the contact 582 away from the post 586 deactivates the motor 360 and, by extension, pump 420. The force imposed by fingers 606 thus returns the trigger 561 to the at rest, off, position.

The speed of the pump is set by the setting of switch 562. The switch 562 can be set to place contact 576 in physical contact with either post 556 or 560. The potential applied to the motor 360, the speed of the pump 420, is a function of which post 556 or 560 is in contact with contact 460

The on/off state and draw rate of through the suction drawing components of the lavage unit is controlled by the suction source 61. Thus the on/off state and draw rate through suction tube 730 is independent of the extent to which irrigating fluid is discharged from the lavage unit 50. As previously mentioned the lumen 736 through the suction tube 730 is crescent shape. The cross width of the lumen of a suction tube in which there is a coaxially extending irrigation tube is equal to one half the inner diameter of the suction tube minus the outer diameter of the irrigation tube. Tip assembly 650 of this disclosure is constructed so suction tube 750 extends along an axis that is laterally offset from the axis through the center of the suction tube 730. Consequently, the cross width of the lumen in the areas of its maximum width is greater than that of the cross width through the suction lumen above-described conventional tip assembly. This increase in cross width through the suction lumen reduces the likelihood that solid and semi-solid wastes drawn through the suction tube 730 will clog the tube.

The waste stream flows out the suction tube 730 into the void space 725 internal to tip assembly head 722. Ribs 708, 710, 712, 714 direct the waste stream towards the inlet opening into suction fitting 702. This reduces the incidence of turbulence within the head void space 725.

Further, once the waste is drawn into the handpiece 64, the waste flows through first through channel 508 and then through channel 506 in the pump housing 422. Channels 506 and 508 are both D-shaped in cross section. Pump housing 422 is further formed so that the widest sections of the channels 506 and 508 are the portions of the channels that are contiguous with and partially overlap each other. This feature of the disclosure reduces the likelihood that the waste can clog within the pump housing 422 as the flow path laterally shifts through the housing. This shift, it is understood is from an axis that is located along the midplane of vertical plane through the housing to an axis that is laterally to one side of this midplane.

When suction is applied and spray shield 770 fitted to the tip body, spray shield ports 790 function as bleed ports. Spray shield stem 772 covers the suction tube notches 734 so there is essentially minimal loss of suction through these notches. When the tip body, without the spray shield is applied to the patient, tip body notches 734 function as bleed ports. The flow of air through the bleed ports prevents the drawing in of the exposed unsevered tissue into the handpiece 64.

V. First Alternative Construction

Figure 33:
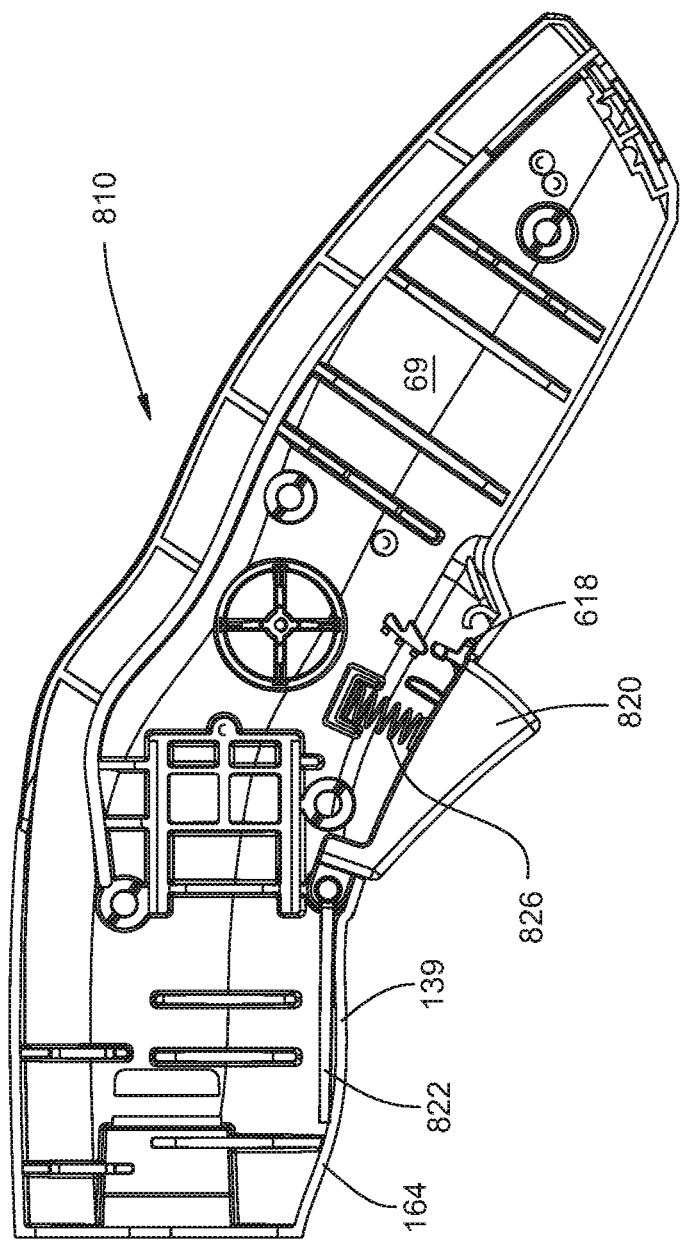
FIG. 33 is a plane view of alternative right side shell of this disclosure with an alternative trigger.

An alternative right side shell 810 of this disclosure is seen in FIG. 33. Right side shell 810 has many of the features of the above described right side shell 70. Accordingly, these features are not redescribed. The right side shell 810 is further formed to have a beam 812 that projects inwardly from the shell base 69. Beam 812 is located forward of bracket 122. Shell 810 is shaped so that beam 812 is a three sided structure that is arranged so that what appear as the base of the beam is directed towards notch 140.

Figure 34:
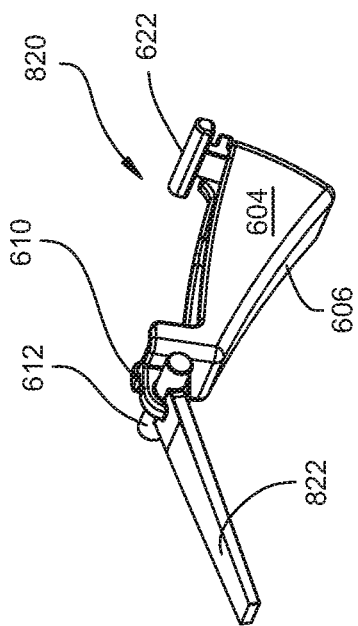
FIG. 34 is perspective view of the alternative trigger of FIG. 33.

FIG. 34 depicts an alternative trigger 820. The trigger 820 has many of the same structural components as previously described trigger 561. Trigger 820 is not formed with fingers that extend over the side panels 604. Instead, the trigger 820 is formed with a single flexible beam 822 that is generally planar in shape. Beam 822 extends forward from tab 610 and lies in a plane perpendicular to the plane of tab 610. The opposed side edges of finger 882 are inwardly tapered. Thus the width across the finger 822 decreases along forward of tab 610.

Returning to FIG. 33, it can be seen that the trigger 820 is mounted to the shells forming the handpiece the same way trigger 561 is mounted to the shells. The opposed ends of beam 612 are seated in the bores internal to shell bosses 164 and 316. In this version of the disclosure a spring 826, seen only FIG. 33, extends from the base of beam 812 into the trigger 820 so as to be located between the trigger sidewalls 604. The base of the spring 826 seats against the inner surface of trigger bottom panel 606. Spring 826 holds the trigger 820 in the off position.

The force spring 826 imposes on the trigger 820 can be overcome by the manual depression of the trigger. When the trigger is moved upwardly, trigger beam 822 is pressed against rims 139 and 312 integral with, respectively, shells 810 and 210. The abutment of finger 822 against the shells 210 and 810 places a force on the trigger 820 in opposition to the manually applied force. The damping of the manual force reduces the likelihood that the practitioner through the inadvertent application of a large force, immediately set the trigger in the constant on state. In some versions of the disclosure, the resistance of the beam 822 to return to the unflexed state provides the force that returns the trigger to the off state.

VI. Further Alternative Embodiments

Alternative versions of the disclosure are possible. For example, there is no requirement that all versions of the disclosure include each of the above described features. Thus the tip assembly with asymmetrically positioned suction and irrigation tubes may be practiced with handpieces other than the described handpiece. Likewise, the described handpiece need not always be used with the described tip assembly.

In alternative versions of the disclosure pump housing 422 may not be provided with cap 492. In these versions of the disclosure the opening into neck is closed by first molding an extension over the neck when the pump housing is formed. A heat stake process is then used to shape the extension to form a cap.

It should further be understood that while the lavage unit of this unit may be include pumps different than the described pump that discharges pulses of irrigating fluid. For example, the handpiece may be provided with a pump that delivers a continuous stream of irrigating fluid. Likewise, in some versions of the disclosure, the pump may be in a console that is spaced from the handpiece. In these versions of the disclosure, the trigger and speed control assemblies are still present. The signals generated be these assemblies are applied over a cable to a control module internal to the console. Based on these signals the control module regulates both the on/off state of the pump and the pump operating rate.

In versions of the disclosure wherein a spring holds and returns the trigger to the off position, components like fingers 605 and beam 822 may be omitted. Similarly, in versions of the disclosure where fingers 605 and/or beam 822 are present the need to provide metal spring may be omitted. Further in some versions of the disclosure the handpiece and trigger may be designed so that gravity provides some or all of the biasing force that, when the trigger is the pump momentary on position, in the absence of a manually applied force, returns the trigger to the pump off position. In these and other versions of the disclosure the handpiece itself would not have an actually biasing member that performs this function. In some versions of the disclosure, the biasing member may be a component separate from the trigger. This biasing member may be a section of elastomeric material or a spring.

Also, there may be versions of the disclosure that do not include conduits through which suction is drawn away from the site to which the lavage unit is applied.

Likewise the trigger and handpiece may have different components that are shaped so that: when the trigger engages a first feature of the handpiece, the trigger causes the pump to be actuated and wherein the biasing force applied to the trigger is able to move the trigger to the off position; and when the trigger engages a second feature of the handpiece, the trigger causes the pump to be actuated and the biasing force applied to the trigger is not able to move the trigger from that position. In some versions of the disclosure it may be desirable to design the handpiece and trigger so that, when the trigger is moved from the off position to a first pump on position the trigger engages a feature of the handpiece that holds the trigger in the on position and that the biasing force applied to the trigger does not dislodge the trigger from that position. Thus, the trigger is in the toggled, constant on position. Then, when the trigger is moved from the first pump on position to a second pump on position, the trigger continues to hold the pump in the state yet the biasing force applied to the trigger is able to move the trigger to the pump off position. In these versions of the disclosure the trigger may not when in both positions engage static components of the handpiece.

Further in some versions of the disclosure, the flexible components that hold the trigger in one or both of the momentary on or toggled (constant) on positions may be mounted to the handpiece. These features, for example, may be spring like members mounted to the handpiece. In these versions of the disclosure, the trigger may not have any flexible components.

Alternative methods of attaching the spray shield to the tip assembly are also possible. For example, in some versions of the disclosure the distal end of the tip is provided with an outwardly extending rib that extends at least partially if not completely circumferentially around the tip. The spray shield is formed so that internal to the stem there is a groove that projects outwardly from the inner surface of the stem that defines the void space in which the tip is inserted. When the spray shield is fitted to the tip assembly, the stem is positioned so that the tip assembly rib seats in this groove.

In some versions of the disclosure the fitting through which irrigating fluid is discharged into the tip assembly irrigation tube 750 and/or the fitting through which the suction is drawn from the tip assembly suction tube 730 may be part of the handpiece. A single surface may replace the ribs integral with the irrigation fitting 750 that direct the surrounding waste stream towards the suction fitting 702.

Likewise the means by which the tip assembly 650 is removably attached to the handpiece may vary from has been described. Thus the components that perform the locking function of legs 654 and feet 660 may be part of the handpiece. In these versions of the disclosure, the tip assembly is formed with components against which the handpiece locking components seat.

Other tip assemblies of this disclosure may be arranged so that while the irrigation tube is disposed in the suction tube, the arrangement of the tubes does not provide the suction tube with a lumen that, in cross section, is crescent shaped. For example is some versions of the disclosure, the tip assembly may be formed so that lumen of the suction tube has a shape that, in cross section, is not crescent shaped. This lumen would at its widest region be greater in width than the cross sectional diameter of the associated irrigation tube. Thus generally in this disclosure, when the irrigation tube is disposed in the suction tube, the lumen of the suction tube has a shape in cross section that is not that of ring with constant inner and outer diameters. Alternatively one or more webs that extend from the inner surface of the suction tube that defines the suction lumen may hold the irrigation tube in the suction tube.

As mentioned above the inventive features of the tip assembly of this disclosure may be used with handpieces other than the described handpiece 64. Thus, the tip assembly may be used with any handpiece that includes an irrigation tube through which irrigating fluid is supplied and a suction tube through which a suction is drawn. These handpieces include powered surgical tools to which a pump is removably attached. Two such irrigating handpieces are disclosed in the Applicant's PCT Pat. App. No. PCT/US2013/059669, the contents of which are published in WO 2014/043475 A1/US Pat. Pub. No. 2015/0182685 and that are now explicitly incorporated herein by reference.

Therefore, it is an object of the appended claims to cover all such modifications and variations that come within the true spirit and scope of the disclosure.

The invention claimed is:

1. A lavage unit comprising:
a handpiece having a distal end;
an irrigation fitting located adjacent said distal end of said handpiece, said irrigation fitting having a bore that extends through a plate from which the irrigating fluid is discharged;
a suction fitting located adjacent said distal end of the handpiece, said suction fitting having a bore that extends through said plate from which suction is drawn;
a tip assembly having a tip suction tube including a suction lumen and a tip irrigation tube, wherein said tip suction tube couples to a suction tube through said bore and said tip irrigation tube has a proximal end dimensioned to engage with and receive fluid discharged from said irrigation fitting;
wherein said tip assembly further includes a void space that is located between said tip suction tube and said bore of said suction fitting so as to provide for fluid communication between said tip suction tube and said bore of said suction fitting, and
a rib extending into said void space between said bore of said suction fitting and said plate, said rib shaped so as to have a distal end and is coupled to said plate such that said distal end is located forward of said bore of said suction fitting; and
wherein said rib is shaped so that the rib extends distally away from the suction fitting.

2. The lavage unit of claim 1, wherein said rib comprises two or more spaced apart ribs; and
wherein said two or more ribs are shaped so that said ribs extend distally away from the suction fitting, and each of said ribs tapers distally away from said suction fitting bore toward a wall of the tip assembly suction tube of said suction tube lumen to direct the waste stream towards said bore of said suction fitting.

3. The lavage unit of claim 2, wherein said irrigation fitting extends distally forward of said suction fitting and said ribs extend outwardly from the irrigation fitting.

4. The lavage unit of claim 2, wherein said two or more ribs extend forward from a portion of a connector for connecting the tip assembly to the handpiece.

5. The lavage unit of claim 2, wherein said two or more ribs are present in a proximal end of said tip assembly suction tube.

6. The lavage unit of claim 1, wherein said tip assembly is further formed so that said tip irrigation tube is disposed in said tip assembly suction tube.

7. The lavage unit of claim 6, wherein said tip irrigation tube is disposed in said tip suction tube so that said tip assembly irrigation tube is centered on a longitudinal axis that is laterally spaced from a longitudinal axis of said tip assembly suction tube.

8. The lavage unit of claim 1, wherein:
said tip assembly is formed so that said tip suction tube and said tip assembly irrigation tube each have a distal end;
a spray shield extends forward from the tip assembly, the spray shield having a head that defines a void space located forward of said distal ends of said tip suction tube and said tip assembly irrigation tube; and
wherein said spray shield is removably attached to said tip assembly.

9. The lavage unit of claim 1, further comprising an irrigation tube extending from a source of irrigating fluid to said bore of said irrigation fitting; and
wherein a pump is disposed in said handpiece for pumping irrigating fluid from said irrigation tube into and out of said tip irrigation tube.

10. The lavage unit of claim 9, wherein a control assembly for regulating actuation of said pump is mounted to said handpiece, said control assembly including a trigger that is moveably mounted to said handpiece and manually actuated for controlling the actuation of said pump;
wherein said control assembly and said trigger are collectively configured so that said trigger has:
a first position in which said control assembly holds said pump in an off state;
a second position in which said control assembly causes said pump to go into the on state wherein said trigger transitions from said first position to said second position when a manual force is applied to said trigger and, upon the removal of the manual force, returns to said first position; and
a third position in which said control assembly actuates said pump and wherein once said trigger is moved to the third position remains in the third position until a disengaging force is applied to said trigger to move said trigger to at least one of said first position or said second position.

11. The lavage unit of claim 1, wherein at least one of said handpiece or said tip assembly includes a feature that facilitates removable attachment of said tip assembly to said handpiece.

12. The lavage unit of claim 1, further comprising a suction tube that extends from said bore of said suction fitting towards a suction source.

13. The lavage unit of claim 1, wherein one end of said rib is tangent to the bore of the suction fitting; and
wherein said rib is angled toward said tip irrigation tube such that said distal end of said rib is adjacent said tip suction tube to direct the waste stream flowing from the tip suction lumen toward said bore of said suction fitting.

14. A lavage unit comprising:
a handpiece having a distal end;
an irrigation fitting located adjacent said distal end of said handpiece, said irrigation fitting having a bore that extends through a plate from which the irrigating fluid is discharged;

a suction fitting located adjacent said distal end of the handpiece, said suction fitting having a bore that extends through said plate from which suction is drawn;

a tip assembly having a tip suction tube including a suction lumen and a tip irrigation tube, wherein said tip suction tube couples to a suction tube through said bore and said tip irrigation tube has a proximal end dimensioned to engage with and receive fluid discharged from said irrigation fitting;

wherein said tip assembly further includes a void space that is located between said tip suction tube and said bore of said suction fitting so as to provide for fluid communication between said tip suction tube and said bore of said suction fitting, and a rib extending into said void space between said bore of said suction fitting and a wall of the tip suction tube, said rib shaped so as to have a distal end and is coupled to the plate such that said distal end is located forward of said bore of said suction fitting; and wherein said rib is shaped so that the rib extends distally away from the suction fitting and terminates at a location adjacent the bore of said suction fitting.

15. The lavage unit of claim 14, wherein said rib comprises two or more spaced apart ribs; and wherein said two or more ribs are shaped so that said ribs extend distally away from the suction fitting, and each of said ribs tapers distally away from said suction fitting bore toward said wall of the tip assembly suction tube of said suction tube lumen to direct the waste stream towards said bore of said suction fitting.

16. The lavage unit of claim 15, wherein said irrigation fitting extends distally forward of said suction fitting and said ribs extend outwardly from the irrigation fitting.

17. The lavage unit of claim 15, wherein said two or more ribs extend forward from a portion of a connector for connecting the tip assembly to the handpiece.

18. The lavage unit of claim 15, wherein said two or more ribs are present in a proximal end of said tip assembly suction tube.

19. The lavage unit of claim 14, wherein said tip assembly is further formed so that said tip irrigation tube is disposed in said tip assembly suction tube; and wherein said tip irrigation tube is disposed in said tip suction tube so that said tip assembly irrigation tube is centered on a longitudinal axis that is laterally spaced from a longitudinal axis of said tip assembly suction tube.

20. The lavage unit of claim 14, wherein at least one of said handpiece or said tip assembly includes a feature that facilitates removable attachment of said tip assembly to said handpiece.

21. The lavage unit of claim 14, wherein one end of said rib is tangent to the bore of the suction fitting; and wherein said rib is angled toward said tip irrigation tube such that said distal end of said rib is adjacent said tip suction tube to direct the waste stream flowing from the tip suction lumen toward said bore of said suction fitting.

* * * * *